United States Patent
Haviv et al.

(10) Patent No.: US 9,901,299 B2
(45) Date of Patent: Feb. 27, 2018

(54) ACTIVATING FUNCTIONAL ELECTRICAL STIMULATION OF ABDOMINAL MUSCLES TO ASSIST COUGHING

(71) Applicants: Yeda Research and Development Co. Ltd., Rehovot (IL); Mor Research Applications Ltd., Tel-Aviv (IL)

(72) Inventors: Lior Haviv, Rehovot (IL); Noam Sobel, Jaffa (IL); Amiram Catz, Kfar-Saba (IL); Itzhak Glass, Hod-HaSharon (IL); Anton Plotkin, Rehovot (IL); Aharon Weissbrod, Rehovot (IL); Sagit Shushan, Rehovot (IL)

(73) Assignees: Yeda Research and Development Co. Ltd., Rehovot (IL); Mor Research Applications Ltd., Tel-Aviv (IL)

( * ) Notice: Subject to any disclaimer, the term of this patent is extended or adjusted under 35 U.S.C. 154(b) by 0 days.

(21) Appl. No.: 15/102,588

(22) PCT Filed: Dec. 9, 2014

(86) PCT No.: PCT/IL2014/051076
§ 371 (c)(1),
(2) Date: Jun. 8, 2016

(87) PCT Pub. No.: WO2015/087324
PCT Pub. Date: Jun. 18, 2015

(65) Prior Publication Data
US 2016/0310068 A1    Oct. 27, 2016

Related U.S. Application Data

(60) Provisional application No. 61/913,462, filed on Dec. 9, 2013.

(51) Int. Cl.
*A61N 1/00* (2006.01)
*A61B 5/00* (2006.01)
(Continued)

(52) U.S. Cl.
CPC .......... *A61B 5/4836* (2013.01); *A61B 5/0492* (2013.01); *A61B 5/087* (2013.01);
(Continued)

(58) Field of Classification Search
CPC .............. A61N 1/36003; A61N 1/3601; A61N 1/36014; A61N 1/36017; A61B 5/0488;
(Continued)

(56) References Cited

U.S. PATENT DOCUMENTS

| 5,190,036 | A | | 3/1993 | Linder | |
|---|---|---|---|---|---|
| 5,397,337 | A | * | 3/1995 | Jaeger | A61N 1/3601 607/62 |
| 2003/0199780 | A1 | * | 10/2003 | Page | A61B 5/0816 600/538 |

FOREIGN PATENT DOCUMENTS

| WO | WO 2010/122560 | 10/2010 |
|---|---|---|
| WO | WO 2015/087324 | 6/2015 |

OTHER PUBLICATIONS

International Preliminary Report on Patentability dated Jun. 23, 2016 From the International Bureau of WIPO Re. Application No. PCT/IL2014/051076.

(Continued)

*Primary Examiner* — Mallika D Fairchild

(57) ABSTRACT

A system for assisted coughing includes a first sensor for measuring a parameter which can indicate a closed glottis and producing a first signal, a processor for receiving the first signal, determining a state indicating the closed glottis and generating an instruction for a Functional Electric Stimulation (FES) controller based, at least in part, on the (Continued)

determining, and a FES controller for generating an electric stimulation signal.

22 Claims, 12 Drawing Sheets

(51) Int. Cl.
- A61B 5/087 (2006.01)
- A61B 5/11 (2006.01)
- A61N 1/36 (2006.01)
- A61B 5/0492 (2006.01)
- A61B 5/0488 (2006.01)
- A61B 5/08 (2006.01)
- G06F 3/01 (2006.01)

(52) U.S. Cl.
CPC .......... *A61B 5/0816* (2013.01); *A61B 5/0823* (2013.01); *A61B 5/1103* (2013.01); *A61B 5/7282* (2013.01); *A61N 1/3601* (2013.01); *A61N 1/36003* (2013.01); *A61N 1/36014* (2013.01); *A61B 5/0488* (2013.01); *A61B 5/0806* (2013.01); *A61B 5/7475* (2013.01); *A61N 1/36017* (2013.01); *G06F 3/012* (2013.01)

(58) Field of Classification Search
CPC ... A61B 5/0492; A61B 5/0806; A61B 5/0816; A61B 5/0823; A61B 5/087; A61B 5/1103; A61B 5/7475
See application file for complete search history.

(56) References Cited

OTHER PUBLICATIONS

International Search Report and the Written Opinion dated Mar. 23, 2015 From the International Searching Authority Re. Application No. PCT/IL2014/051076.
Bozic et al. "Detection of Breathing Phases", Serbian Journal of Electrical Engineering, 6(3): 389-398, Dec. 2009.
De Troyer et al. "Mechanism of Active Expiration in Tetraplegic Subjects", The New England Journal of Medicine, 314(12): 740-744, Mar. 20, 1986.
Estenne et al. "Cough in Tetraplegic Subjects: An Active Process", Annals of Internal Medicine, 112: 22-28, 1990.
Estenne et al. "Effects of Abdominal Strapping on Forced Expiration in Tetraplegic Patients", American Journal of Respiratory and Critical Care Medicine, 157: 95-98, 1998.
Frost "Spinal Cord Injury Medicine", Physical Medicine and Rehabilitation, Chap.55: 1230-1282, 2000.
Fujiwara et al. "Expiratory Function in Complete Tetraplegics. Study of Spirometry, Maximal Expiratory Pressure, and Muscle Activity of Pectoralis Major and Latissimus Dorsi Muscles", American Journal of Physical Medicine & Rehabilitation, 78(15): 464-469, 1999.
Gollee et al. "A Control System for Automatic Electrical Stimulation of Abdominal Muscles to Assist Respiratory Function in Tetraplegia", Medical Engineering & Physics, XP022055527, 29(7): 799-807,May 3, 2007. Abstract, Section 2, Lines 21-31, Section 2.1(1), p. 801, Fig.3.
Gollee et al. "Abdominal Stimulation for Respiratory Support in Tetraplegia: A Tutorial Review", Journal of Automatic Control, University of Belgrade, 18(2): 85-92, 2008.
Gollee et al. "An SSVEP-Based Brain-Computer Interface for the Control of Functional Electrical Stimulation", IEEE Transactions on Biomedical Engineering, XP011343307, 57(8): 1847-1855, Aug. 2010. Abstract, Section II.C, II.D, Table II.
Gollee et al., "Automiatic Electrical Stimulation of Abdominal Wall Muscles Increases Tidal Volume and Cough Peak Flow in Tetraplegia", Technology and Health Care, XP055175145, 16(4): 273-281, Oct. 29, 2008. Section 2.2, Lines 7, 13-14, 20-31, 36-38, Section 2.3, Lines 16-17.
Guyton et al. "Pulmonary Ventilation", Textbook of Medical Physiology, Chap.37: 477-489, 1996.
Jaeger et al. "Cough in Spinal Cord Injured Patients: Comparison of Three Methods to Produce Cough", Archives of Physical Medicine and Rehabilitation, 74(12): 1358-1361, Dec. 1993.
Kathiresan et al. "A Review of Abdominal Muscle Stimulation for Patients With Spinal Cord Injury", Journal of Physical Therapy Science, 22(4): 455-464, 2010.
Linder "Functional Electrical Stimulation to Enhance Cough in Quadriplegia", Chest, 103: 166-169, 1993.
Plotkin et al. "Sniffing Enables Communication and Environmental Control for the Severly Disabled", Proc. Natl. Acad. Sci. USA, PNAS, 107(32): 14413-14418, Aug. 10, 2010.
Sivasothy et al. "Effect of Manually Assisted Cough and Mechanical Insufflation on Cough Flow of Normal Subjects, Patients With Chronic Obstructive Pulmonary Disease (COPD), and Patients With Respiratory Muscle Weakness", Thorax, 56: 438-444, 2001.
Spivak et al. "Electromyographic Signal-Activated Functional Electrical Stimulation of Abdominal Muscles: The Effect on Pulmonary Function in Patients With Tetraplegia", Spinal Cord, XP055175401, 45(7): 491-495, Feb. 27, 2007. Abstract, Section "Introduction", Lines 54-62, Section "Methods", Lines 33-42, Section "Discussion", Lines 7-17.
Stanic et al. "Functional Electrical Stimulation of Abdominal Muscles to Augment Tidal Volume in Spinal Cord Injury", IEEE Transactions on Rehabilitation Engineering, 8(1): 30-34, Mar. 2000.
Taylor et al. "Electrical Stimulation of Abdominal Muscles for Control of Blood Pressure and Augmentation of Cough in a C3/4 Level Tetraplegic", Spinal Cord, 40: 34-36, 2002.
Zupan et al. "Effects of Respiratory Muscle Training and Electrical Stimulation of Abdominal Muscles on Respiratory Capabilities in Tetraplegic Patients", Spinal Cord, 35: 540-545, 1997.

* cited by examiner

ACTIVATING FUNCTIONAL ELECTRICAL STIMULATION OF ABDOMINAL MUSCLES TO ASSIST COUGHING

RELATED APPLICATIONS

This application is a National Phase of PCT Patent Application No. PCT/IL2014/051076 having International filing date of Dec. 9, 2014, which claims the benefit of priority under 35 USC § 119(e) of U.S. Provisional Patent Application No. 61/913,462 filed on Dec. 9, 2013. The contents of the above applications are all incorporated by reference as if fully set forth herein in their entirety.

FIELD AND BACKGROUND OF THE INVENTION

The present invention, in some embodiments thereof, relates to methods and systems for using nasal airflow to activate Functional Electrical Stimulation (FES) of abdominal muscles to assist coughing.

Tetraplegic patients cannot cough enough to clear their sputum because of expiratory muscle weakness, mainly of the abdominal muscles. This inability to cough may cause respiratory complications, such as pneumonia and atelectasis, and are major causes of mortality and inhibit rehabilitation programs in spinal cord injury. People with tetraplegia depend on a caregiver applying manual pressure intermittently to the anterior abdominal wall in order to induce assisted coughing.

Prof. A. Catz and his team at Lowenstein Hospital—Rehabilitation Center have developed an EMG-activated stimulation system for abdominal stimulation independent of a caregiver. Stimulation for cough was triggered by EMG signals obtained from either the pectoralis major muscle or the deltoid. While it would be expected that FES greatly improve coughing ability, their data did not support such an optimistic conclusion.

Additional background art includes:

Published PCT Patent Application WO 2010/122560 of Sobel et al, filed Apr. 22, 2010, which describes a method of receiving input from a user, comprising measuring a nasal air parameter and generating an instruction for one or both of a device and controller based on said measurement.

An article by De Troyer A, Estenne M, Heilporn A., titled "Mechanism of active expiration in tetraplegic subjects", published in N Engl J Med 1986; 314: 740-744.

An article by Estenne M, De Troyer A., titled "Cough in tetraplegic subjects: an active process", published in Ann Intern Med 1990; 112: 22-28.

An article by Estenne M, Van Muylem A, Gorini M, Kinnear W, Heilporn A, De Troyer A., titled "Effects of abdominal strapping on forced expiration in tetraplegic patients", published in Am J Respir Crit Care Med 1998; 157: 95-98.

An article by Frederick S F, titled "Spinal Cord Injury Medicine", published in Phys Med Rehabil, Braddom L R (ed), W B Saunders, Philadelphia 2000, pp 1248.

An article by Fujiwara T, Yukiriho H, Chino N., titled "Expiratory Function in complete tetraplegics" published in Am J Phys Med Rehabil 1999; 78: 464-469.

An article by Guyton A C, Hall J E (eds), titled "Pulmonary ventilation" published in Textbook of medical physiology. WB Saunders, Philadelphia 1996, pp 477-489.

An article by Jaeger R J, Turba R M, Yarkony G M, Roth E J, titled "Cough in spinal cord injured patients: comparison of three methods to produce cough", published in Arch Phys Med Rehabil 1993; 74: 1358-1361.

An article by Linder S H, titled "Functional electrical stimulation to enhance cough in quadriplegia", published in Chest 1993; 103: 166-169.

An article by Plotkin A, Sela L, Weissbrod A, Kahana R, Haviv L, Yeshurun Y, Soroker N, Sobel N., titled "Sniffing enables communication and environmental control for the severely disabled", published in PNAS 2010; 107: 14413-14419.

An article by Sivasothy P, Brown L, Smith I E, Shneerson J M, titled "Effect of manually assisted cough and mechanical insufflation on cough flow of normal subjects, patients with chronic obstructive pulmonary disease (COPD), and patients with respiratory muscle weakness", published in Thorax 2001; 56: 438-444.

An article by Spivak E, Keren O, Niv D, Levental J, Steinberg F, Barak D, Chen B, Zupan A, Catz A., titled "Electromyographic signal-activated functional electrical stimulation of abdominal muscles: the effect on pulmonary function in patients with tetraplegia" published in Spinal Cord 2007; 45: 491-495.

An article by Stanic U, Kandare F, Jaeger R, Sorli J., titled "Functional electrical stimulation of abdominal muscles to augment tidal volume in spinal cord injury", published in IEEE Trans Rehabil Eng 2000; 8: 30-34.

An article by Taylor P N, Tromans A M, Haris K R, Swain I D, titled "Electrical stimulation of abdominal muscles for control of blood pressure and augmentation of cough in a C3/C4 level tetraplegic", published in Spinal Cord 2002; 40: 34-36.

An article by Zupan A et al., titled "Effects of respiratory muscle training and electrical stimulation of abdominal muscles on respiratory capabilities in tetraplegic patients", published in Spinal Cord 1997; 35: 540-545.

An article by Gollee H et al., titled "Abdominal stimulation for respiratory support in tetraplegia: a tutorial review", published in Journal Of Automatic Control, University Of Belgrade 2008; 18(2): 85-92.

An article by Božic I, Klisic D, Savic A, titled "Detection of Breathing Phases", published in Serbian Journal Of Electrical Engineering 2009; 6(3): 389-398.

An article by Gollee H et al., titled "A control system for automatic electrical stimulation of abdominal muscles to assist respiratory function in tetraplegia", published in Medical Engineering & Physics 2007; 29: 799-807.

An article by Kathiresan G et al., titled "A Review of Abdominal Muscle Stimulation for Patients with Spinal Cord Injury", published in Journal of Physical Therapy Science 2010; 22(4): 455-464.

The disclosures of all references mentioned above and throughout the present specification, as well as the disclosures of all references mentioned in those references, are hereby incorporated herein by reference.

SUMMARY OF THE INVENTION

According to some embodiments of the present invention, methods and systems are taught for using nasal airflow to activate Functional Electrical Stimulation (FES) of abdominal muscles to assist coughing.

Patients who need assistance with coughing, such as patients whose abdominal muscles may not be under their full control, can benefit from FES of the abdominal muscles to assist coughing, for example to clear their airways.

In some embodiments a patient uses nasal airflow to control initiation of FES of the abdominal muscles to assist coughing.

In some embodiments a patient's nasal airflow is monitored, and nasal airflow typical of an oncoming cough may be used to control initiation of FES of the abdominal muscles to assist the oncoming cough.

According to an aspect of some embodiments of the present invention there is provided a system for assisted coughing including a first sensor for measuring a parameter which can indicate a closed glottis and producing a first signal, a processor for receiving the first signal, determine a state indicating the closed glottis and generating an instruction for a Functional Electric Stimulation (FES) controller based, at least in part, on the determining, and a FES controller for generating an electric stimulation signal.

According to some embodiments of the invention, the processor is further configured for detecting a command input, and to attempt to determine the state indicating the closed glottis following the command input.

According to some embodiments of the invention, the first sensor includes a nasal air sensor configured for sensing the patient's nasal air flow.

According to some embodiments of the invention, further including a second sensor configured to accept the command input.

According to some embodiments of the invention, the second sensor is configured to accept the command input from a patient. According to some embodiments of the invention, the second sensor is configured to accept the command input from a caregiver.

According to some embodiments of the invention, the second sensor includes the same nasal air sensor configured for sensing the patient's nasal air flow.

According to some embodiments of the invention, the second sensor includes at least one patient command sensor selected from a group including an eye blink sensor, a microphone, an electromyography (EMG) electrode configured for sensing the patient's EMG activity of the neck muscles, a chest belt for monitoring respiration, and an electrophysiological sensor for sensing abdominal muscles.

According to some embodiments of the invention, the processor is configured to analyze the first signal from the nasal air sensor and generate the instruction for the FES controller based, at least in part, on the analysis.

According to some embodiments of the invention, the processor determines a state of closure of a glottis based, at least in part, on detecting a start of a plateau in the nasal air signal.

According to some embodiments of the invention, the processor produces the instruction for the FES controller when the processor detects a slope in the nasal air signal followed by a plateau in the nasal air signal, the plateau lasting at least 50 milliseconds.

According to some embodiments of the invention, the plateau is detected by the processor continuously sampling the nasal air signal and detecting a difference between nasal air signal values within the plateau of less than a threshold value.

According to some embodiments of the invention, the slope is fitted to a straight line having a slope $\alpha$, and the plateau is fitted to a straight line having a slope $\beta$, a value of $\alpha$ is below a threshold $T\alpha$, and a value of $\beta$ is below a threshold $T\beta$.

According to some embodiments of the invention, $\alpha$ and $\beta$ are calculated as follows $$\hat{\beta} = \frac{\sum_{i=1}^{n}(x_i - \bar{x})(y_i - \bar{y})}{\sum_{i=1}^{n}(x_i - \bar{x})^2} = \frac{\sum_{i=1}^{n} x_i y_i - \frac{1}{n}\sum_{i=1}^{n} x_i \sum_{j=1}^{n} y_j}{\sum_{i=1}^{n}(x_i^2) - \frac{1}{n}\left(\sum_{i=1}^{n} x_i\right)^2} =$$

$$\frac{\overline{xy} - \bar{x}\bar{y}}{\overline{x^2} - \bar{x}^2} = \frac{\text{Cov}[x, y]}{\text{Var}[x]} = r_{xy}\frac{s_y}{s_x}, \hat{\alpha} = \bar{y} - \hat{\beta}\bar{x},$$

where $r_{xy}$ is a sample correlation coefficient between x and y, $s_x$ is a standard deviation of x, $s_y$ is a standard deviation of y, and a horizontal bar over a variable denotes a sample average of the variable.

According to some embodiments of the invention, the electric stimulation signal includes a same electric stimulation signal to all electrodes receiving the electric stimulation signal.

According to some embodiments of the invention, the electric stimulation signal includes a stimulation signal with a frequency of approximately 100 Hz, including pulse durations of 200 μs.

According to some embodiments of the invention, the electric stimulation signal includes a stimulation signal with a frequency in a range of 30 Hz-200 Hz, including pulse durations of 100 μs-300 μs.

According to some embodiments of the invention, the electric stimulation signal lasts for a period of time in a range of 250 milliseconds to 1250 milliseconds.

According to some embodiments of the invention, further including circuitry for adjusting the FES.

According to some embodiments of the invention, the unit for adjusting the FES adjusts a time of starting the FES. According to some embodiments of the invention, the unit for adjusting the FES adjusts a duration of the FES.

According to some embodiments of the invention, the adjusting the FES includes using feedback to automatically adjust the FES.

According to some embodiments of the invention, the feedback includes a value of at least one parameter selected from a group consisting of a value assigned to the patient's feedback, a value assigned to a medical practitioner' feedback, a value of air flow temperature during a cough which is assisted by the FES, a value of $CO_2$ concentration during a cough which is assisted by the FES, a value of electromyography (EMG) measured during a cough which is assisted by the FES, a value of PEF (Peak Expiratory Flow) of a cough which is assisted by the FES, a value of maximum nasal expiration during the cough which is assisted by the FES, a value of a maximum volume of a sound of the cough which is assisted by the FES, and a value maximum output of lung air of the cough which is assisted by the FES.

According to some embodiments of the invention, the adjusting the FES includes using machine learning to adjust the FES.

According to an aspect of some embodiments of the present invention there is provided a method of assisted coughing including determining when a patient's glottis is expected to be closed, and producing Functional Electric Stimulation (FES) based, at least in part, on the determining.

According to some embodiments of the invention, the determining when the patient's glottis is expected to be closed is based, at least in part, on analyzing a signal from a sensor configured to sense a patient.

According to some embodiments of the invention, the determining when the patient's glottis is expected to be closed is based, at least in part, on analyzing a nasal air signal from a patient's nasal air flow sensor.

According to some embodiments of the invention, the determining when the patient's glottis is expected to be closed is based, at least in part, on determining a start of a plateau in the nasal air signal.

According to some embodiments of the invention, the determining when the patient's glottis is expected to be closed is based, at least in part, on determining a negative slope in the nasal air signal followed by determining a plateau in the nasal air signal, the plateau lasting at least 50 milliseconds.

According to some embodiments of the invention, the determining the plateau is performed by continuously sampling the nasal air signal and determining a difference of less than a threshold value between nasal air signal values within the plateau.

According to some embodiments of the invention, the negative slope is fitted to a straight line having a slope $\alpha$, and the plateau is fitted to a straight line having a slope $\beta$, a value of $\alpha$ is below a threshold $T\alpha$, and a value of $\beta$ is below a threshold $T\beta$.

According to some embodiments of the invention, $\alpha$ and $\beta$ are calculated as follows $$\hat{\beta} = \frac{\sum_{i=1}^{n}(x_i-\bar{x})(y_i-\bar{y})}{\sum_{i=1}^{n}(x_i-\bar{x})^2} = \frac{\sum_{i=1}^{n}x_iy_i - \frac{1}{n}\sum_{i=1}^{n}x_i\sum_{j=1}^{n}y_j}{\sum_{i=1}^{n}(x_i^2) - \frac{1}{n}\left(\sum_{i=1}^{n}x_i\right)^2} =$$

$$\frac{\overline{xy}-\bar{x}\bar{y}}{\overline{x^2}-\bar{x}^2} = \frac{\text{Cov}[x,y]}{\text{Var}[x]} = r_{xy}\frac{s_y}{s_x}, \hat{\alpha}=\bar{y}-\hat{\beta}\bar{x},$$

where $r_{xy}$ is a sample correlation coefficient between x and y, $s_x$ is a standard deviation of x, $s_y$ is a standard deviation of y, and a horizontal bar over a variable denotes a sample average of the variable.

According to some embodiments of the invention, the producing FES includes producing a same electric stimulation signal to all electrodes receiving the electric stimulation signal.

According to some embodiments of the invention, the producing FES includes producing an electric stimulation signal with a frequency of approximately 30-200 Hz, including pulse durations of 100-300 µs.

According to some embodiments of the invention, the producing FES includes producing an electric stimulation signal lasting for a period of time in a range of 250 milliseconds to 1250 milliseconds.

According to some embodiments of the invention, the determining when the patient's glottis is expected to be closed is performed following receipt of a command input.

According to some embodiments of the invention, the receipt of the command input includes receipt of the command input from a processor analyzing a signal from a sensor configured to sense receipt of a command input from the patient.

According to some embodiments of the invention, the receipt of the command input from the patient includes receipt of a command input from the processor analyzing a nasal air signal from a patient's nasal air flow sensor.

According to some embodiments of the invention, the sensor configured to sense receipt of a command input from the patient includes at least one sensor selected from a group including an eye blink sensor, a microphone, an electromyography (EMG) electrode configured for sensing the patient's EMG activity of the neck muscles, a chest belt for monitoring respiration, and an electrophysiological sensor for sensing abdominal muscles.

According to some embodiments of the invention, the receipt of the command input includes receipt of a command input from a caregiver.

According to some embodiments of the invention, further including adjusting the FES.

According to some embodiments of the invention, the adjusting the FES includes adjusting when to start the FES.

According to some embodiments of the invention, the adjusting when to start the FES includes determining an average duration of a patient's closing the glottis, adjusting to start the FES a short period of time prior to an end of the determining when a patient's glottis is expected to be closed.

According to some embodiments of the invention, the adjusting the FES includes adjusting a duration of the FES.

According to some embodiments of the invention, the adjusting the FES includes using feedback to adjust the FES.

According to some embodiments of the invention, the feedback includes at least one parameter selected from a group consisting of a value assigned to the patient's feedback, a value assigned to a medical practitioner' feedback, a value of air flow temperature during a cough which is assisted by the FES, a value of $CO_2$ concentration during a cough which is assisted by the FES, a value of electromyography (EMG) measured during a cough which is assisted by the FES, a value of PEF (Peak Expiratory Flow) of a cough which is assisted by the FES, a value of maximum nasal expiration during the cough which is assisted by the FES, a value of maximum volume of a sound of the cough which is assisted by the FES, and a value of maximum output of lung air of the cough which is assisted by the FES.

According to some embodiments of the invention, the adjusting the FES includes using machine learning to adjust the FES.

According to an aspect of some embodiments of the present invention there is provided a method of providing Functional Electric Stimulation (FES) to assist coughing including detecting an intent to cough in a patient, detecting a time of glottis closure in the patient, providing FES to assist coughing delayed by a period of time following the glottis closure.

According to some embodiments of the invention, the detecting an intent to cough includes detecting a plateau in nasal air flow.

According to some embodiments of the invention, the detecting an intent to cough includes detecting a value of nasal air flow less than a threshold value lasting longer than 50 milliseconds.

According to some embodiments of the invention, the nasal air flow parameters for the detecting an intent to cough consists of a value of a slope of air flow data points during inspiration exceeding a threshold value.

According to some embodiments of the invention, the detecting the time of glottis closure in the patient includes detecting a time when nasal air flow transitions from inspiration to a minimum of air flow.

According to some embodiments of the invention, further including measuring the patient's glottis closure duration over a plurality of breathing cycles by the patient which include glottis closure and coughing, determining a typical glottis closure duration for the patient, providing FES to the patient at a time delayed by the period of time following the glottis closure, the delay being less than the typical glottis closure duration for the patient.

According to some embodiments of the invention, a value for the typical glottis closure duration is determined by averaging glottis closure duration over the plurality of breathing cycles by the patient which included glottis closure and coughing.

According to some embodiments of the invention, the period of time is 20-100 milliseconds less than the typical glottis closure duration for the patient. According to some embodiments of the invention, the period of time is in a range of 10%-30% shorter than the typical glottis closure duration for the patient.

According to some embodiments of the invention, the period of time is adjusted to optimize the patient's cough. According to some embodiments of the invention, a duration of the FES is adjusted to optimize the patient's cough.

According to some embodiments of the invention, optimizing the patient's cough is based on at least one parameter selected from a group consisting of a value assigned to the patient's feedback, a value assigned to a medical practitioner' feedback, a value of air flow temperature during a cough which is assisted by the FES, a value of $CO_2$ concentration during a cough which is assisted by the FES, a value of electromyography (EMG) measured during a cough which is assisted by the FES, a value of PEF (Peak Expiratory Flow) of a cough which is assisted by the FES, a value of maximum nasal expiration during the cough which is assisted by the FES, a value of maximum volume of a sound of the cough which is assisted by the FES, and a value of maximum output of lung air of the cough which is assisted by the FES.

According to an aspect of some embodiments of the present invention there is provided a non-transitory computer-readable medium containing instructions for a method of assisted coughing as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an example embodiment, the software instructions are stored on a non-transitory computer readable storage media. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
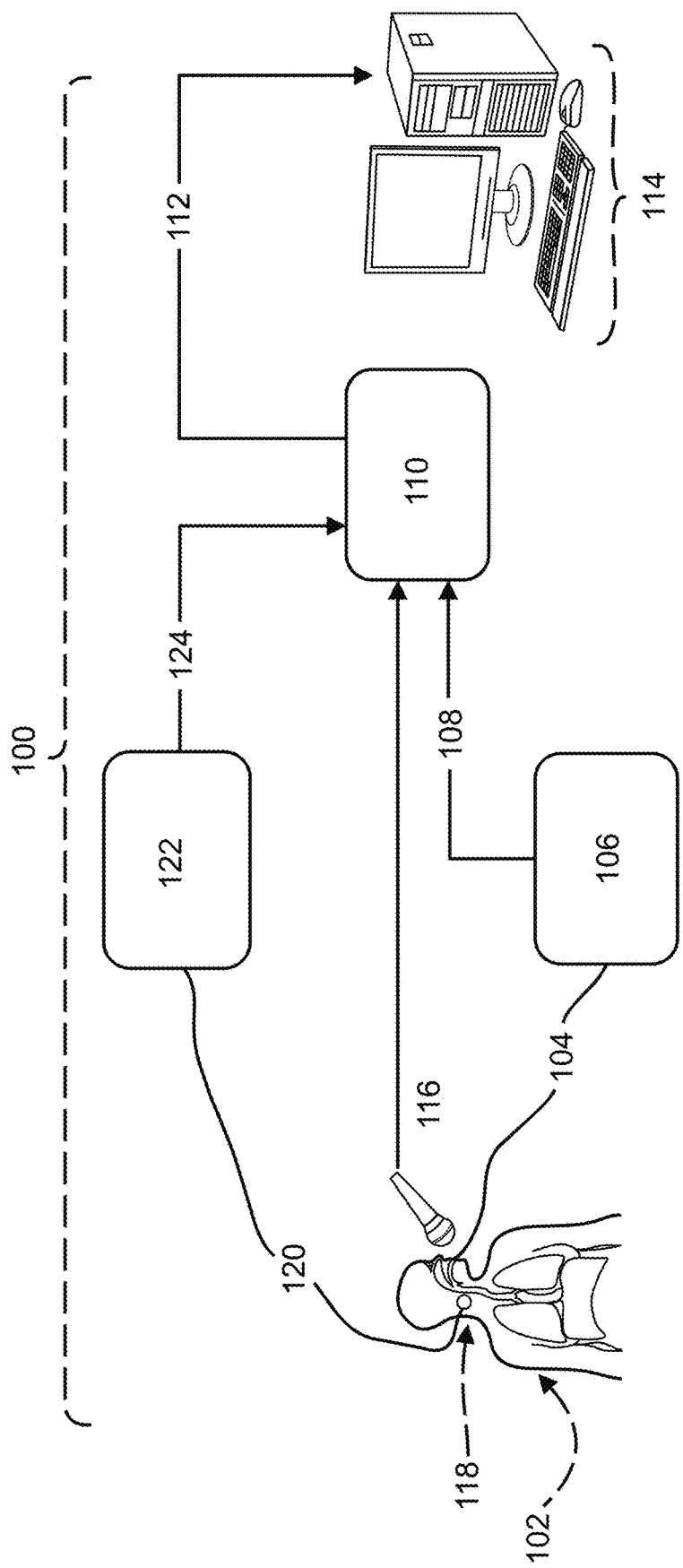
FIG. 1 is a simplified illustration of a system for gathering data from a patient according to an example embodiment of the invention.

The present invention, in some embodiments thereof, relates to methods and systems for using nasal airflow to activate Functional Electrical Stimulation (FES) of abdominal muscles to assist coughing.

Overview

In some cases, such as patients with paralysis, patients find it hard or impossible to cough, to clear their lungs. In such cases, optional FES of abdominal muscles can be useful, assisting the patients in producing an effective cough.

In the above-mentioned article by Gollee H et al., titled "A control system for automatic electrical stimulation of abdominal muscles to assist respiratory function in tetraplegia", apparently stimulation for cough was applied (see FIGS. 3a and 3b of the article) toward and end of inspiration, using two different trigger points, and optionally delaying stimulation by a fixed time following the trigger point. Stimulation was applied for a period of approximately 1.5 seconds (from 31.5 seconds to 33 seconds along the time axis). Such stimulation was tested by the present inventors, and caused an ineffective cough, and a feeling of lack of air by the end of the stimulation. It is assumed that the stimulation was not applied with correct timing, and/or lasted for too long. Air flow was reported to be measured at the mouth, which is an obtrusive method, not considered to be suitable for prolonged use by patients.

In the above-mentioned article by Gollee et al., titled "Abdominal stimulation for respiratory support in tetraplegia: a tutorial review", apparently stimulation for cough was applied (see FIG. 2b of the article) toward and end of inspiration, and stimulation was applied for a period of approximately 1.75 seconds (from 1.5 seconds to approximately 3.25 seconds along the time axis). Such stimulation was tested by the present inventors, and caused an ineffective cough, and a feeling of lack of air by the end of the stimulation. It is assumed that the stimulation was not applied with correct timing, and/or lasted for too long. Air flow was reported to be measured at the mouth, which is an obtrusive method, not considered to be suitable for prolonged use by patients.

In the above-mentioned article by Kathiresan G et al., titled "A Review of Abdominal Muscle Stimulation for Patients with Spinal Cord Injury", apparently stimulation for cough was applied (see FIG. 2b of the article) toward an end of inspiration, and stimulation was applied for a period of approximately 1.75 seconds (from 1.5 seconds to approximately 3.25 seconds along the time axis). Such stimulation was tested by the present inventors, and caused an ineffective cough, and a feeling of lack of air by the end of the stimulation. It is assumed that the stimulation was not applied with correct timing, and/or lasted for too long. Air flow was reported to be measured at the mouth, which is an obtrusive method, not considered to be suitable for prolonged use by patients.

In the above-mentioned article by Božic et al titled "Detection of Breathing Phases", it was suggested that a full face mask might not be used, rather apparently a combination of three signals measured at the mouth: air pressure, air temperature and sound (by microphone).

The inventors presume that the results of applying FES to abdominal muscles, as mentioned above with reference to Professor Catz, have not been positive because activation of the FES was not synchronized with onset of patient glottis closure in order to evoke an effective cough.

An aspect of some embodiments of the invention relates to synchronizing FES of a cough and a patient's breathing and/or residual cough and/or determination of a closed glottis.

An aspect of some embodiments of the invention relates to a duration of FES applied to the patient. In some embodiments the FES is shorter than any apparently described in the references mentioned above, in order to produce a short, explosive, cough rather than a long, forced, expiration of air.

An aspect of some embodiments of the invention relates to smart coughing, in which a patient's needs and/or commands are used to modify parameters used in synchronizing the cough and in producing the cough.

An aspect of some embodiments of the invention relates to a method for providing Functional Electric Stimulation (FES) to assist coughing by detecting an intent to cough in a patient, detecting a time of glottis closure in the patient, and providing FES to assist coughing, optionally at a specific time following the glottis closure.

An aspect of some embodiments of the invention relates to respiratory rehabilitation. A system of assisted coughing as described herein may be used to rehabilitate respiratory action of patients with a weak respiratory action. Use of the system potentially rehabilitates respiratory action in patients.

The inventors have developed a method providing effective synchronization between FES triggering and a patient's breathing and/or residual cough.

In some embodiments, example methods of which are described below, are used to integrate a nasal-air-controlled trigger to activate the FES.

In some embodiments the synchronization is optionally made with sub-second precision.

In some example embodiments of the invention, a patient's nasal air flow is monitored, and the patient can optionally provide a signal to a system to produce FES and cause a cough. In such embodiments, sensors for measuring the nasal airflow are considered potentially less intrusive than measurement systems measuring parameters at the mouth, and are potentially more reliable.

In some embodiments, the signal may be any signal detectable by a system such as described in above-mentioned Published PCT Patent Application WO 2010/122560 of Sobel et al.

In some embodiments the signal detection can optionally generate an instruction for a FES controller to produce FES to the abdomen, in which case the patient has initiated a command to cause a cough. A non-limiting example of such an instruction may optionally be two consecutive sniffs (nasal air signals) by the patient, optionally causing production of a command to cause a cough and/or to assist a natural cough.

In some embodiments the signal detection optionally generates an instruction for activating a FES controller to produce FES to the abdomen, in which case the patient has optionally initiated a command to cause a cough.

In some embodiments the signal detection can optionally detect signs of an oncoming cough, which might be a weak cough, and generate an instruction for a FES controller to produce FES to the abdomen, in which case the weak cough is augmented by the FES.

In some embodiments the signal detection can optionally cause the above-mentioned detection system to start a period of attempting to determine when a cough starts. The patient then initiates a cough, the detection system determines an oncoming cough, and assists in the coughing by initiating the FES to the abdomen. Such a setup can be useful for patients which cannot cough effectively, and provide a command which causes the example embodiment to assist their attempt at coughing.

In some embodiments, various methods of determining a cough based on nasal air signals are used, examples of which are described below.

In some embodiments, various methods and components in addition to monitoring nasal air are used, examples of which are described below.

In some embodiments different FES signals are used to stimulate coughing, examples of which are described below.

In some embodiments different electrode arrangements are used to provide FES signals to the patient's abdomen, examples of which are described below.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the examples. The invention is capable of other embodiments or of being practiced or carried out in various ways.

Integration of Nasal Air Controller Technology and FES

In some embodiments a system is provided which enables computerized control of the FES and incorporates nasal air controller technology for FES triggering.

In some embodiments, software is used to measure the nasal air pressure, and to converts the pressure into electrical signals, which in turn, will be used as a trigger to activate the FES, as illustrated in FIG. 1 and described with reference to FIG. 1.

Nasal air controller technology and FES were integrated using, by way of a non-limiting example, an Arduino microcontroller device. The Arduino microcontroller is an open-source electronics prototyping platform based on flexible, easy-to-use hardware and software, potentially providing a low cost system. The Arduino microcontroller can receive analog inputs from pressure sensors and can be programmed to trigger the FES.

In some embodiments, the system operates in a self-activation mode, with a manual standby button.

Reference is now made to FIG. 1, which is a simplified illustration of a system 100 for gathering data from a patient 102 according to an example embodiment of the invention.

FIG. 1 depicts a patient 102 with a cannula 104 for providing nasal air to one or more sensors 106. In some embodiments the sensors 106 optionally sense nasal air flow. In some embodiments the sensors 106 optionally sense air pressure.

The sensors 106 provide an output signal 108, which in some embodiments—as described above with reference to the Arduino microcontroller—may be analog, and in some embodiments may be digital.

In some embodiments the output signal 108 is optionally provided to a microcontroller 110, such as the above-mentioned Arduino, or an AD Instruments Power Lab unit.

In some embodiments the microcontroller 110 optionally provides output signals 112 to a computer 114, optionally for further processing and/or storage.

In some embodiments the microcontroller 110 optionally accepts input from additional sources of signals which may optionally also serve, alone or in combination with each other and/or with the nasal air signals, to determine an oncoming cough or a patient command.

By way of a non-limiting example, in some embodiments a microphone 116 optionally provides an input signal to the microcontroller 110.

By way of a non-limiting example, in some embodiments, electromyography (EMG) electrodes 118 may optionally be connected to the patient's throat, and provide signals 120 to an optional electrophysiological signal amplifier 122, which optionally provides an output 124 to the microcontroller 110.

Discovering Nasal Breathing Parameters During Coughing

A cough reflex, processed by the medulla, is preceded by a series of events, typically in the following order: (I) air inspiration; (II) tight closure of the glottis to trap the air within the lungs; (III) forceful contraction of abdominal muscles and accessory expiratory muscles; and (IV) a sudden opening of the glottis and outward explosion of the air under pressure.

In some embodiments FES is used to assist the contraction of the abdominal muscles. The contraction of the abdominal muscles optionally comes at a precise, correct timing after closure of the glottis.

The setup described above with reference to FIG. 1 was used to find one or more features in the nasal respiration pattern which can indicate glottis closure. In some embodiments glottis closure is optionally evaluated by glottis electrical activity and electrical activity of other neck muscles during a cough using electromyography (EMG).

In some embodiments a setup for measuring nasal respiration during a cough is used concurrently with measuring EMG activity of the neck muscles as illustrated in FIG. 1.

In some embodiments a setup for measuring nasal respiration during a cough is used concurrently with monitoring a chest belt for monitoring respiration (not shown).

Figure 2:
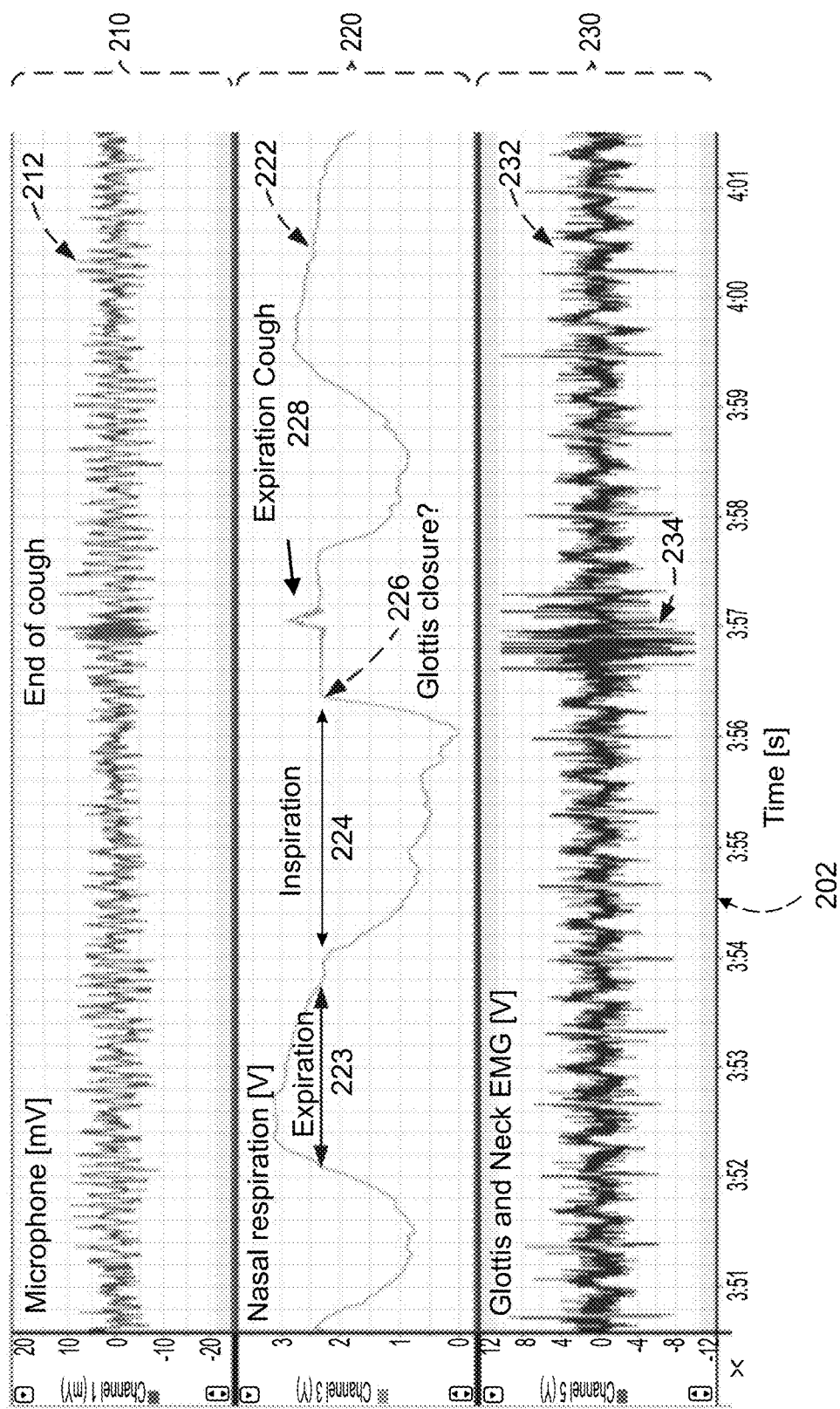
FIG. 2 depicts three graphs showing a microphone signal, nasal air flow and an electromyographic (EMG) signal of glottis and neck muscles as measured by the system of FIG. 1.

Reference is now made to FIG. 2, which depicts three graphs 210 220 230 showing a microphone signal 212, nasal air flow 222 and an electromyographic (EMG) signal 232 of glottis and neck muscles as measured by the system 100 of FIG. 1.

The graphs 210 220 230 all share a common X-axis 202 depicting time.

FIG. 2 depicts a typical nasal respiratory pattern during coughing. It is noted that negative flow corresponds to inspiration 224 while a positive flow indicates expiration 223.

Figure 5:
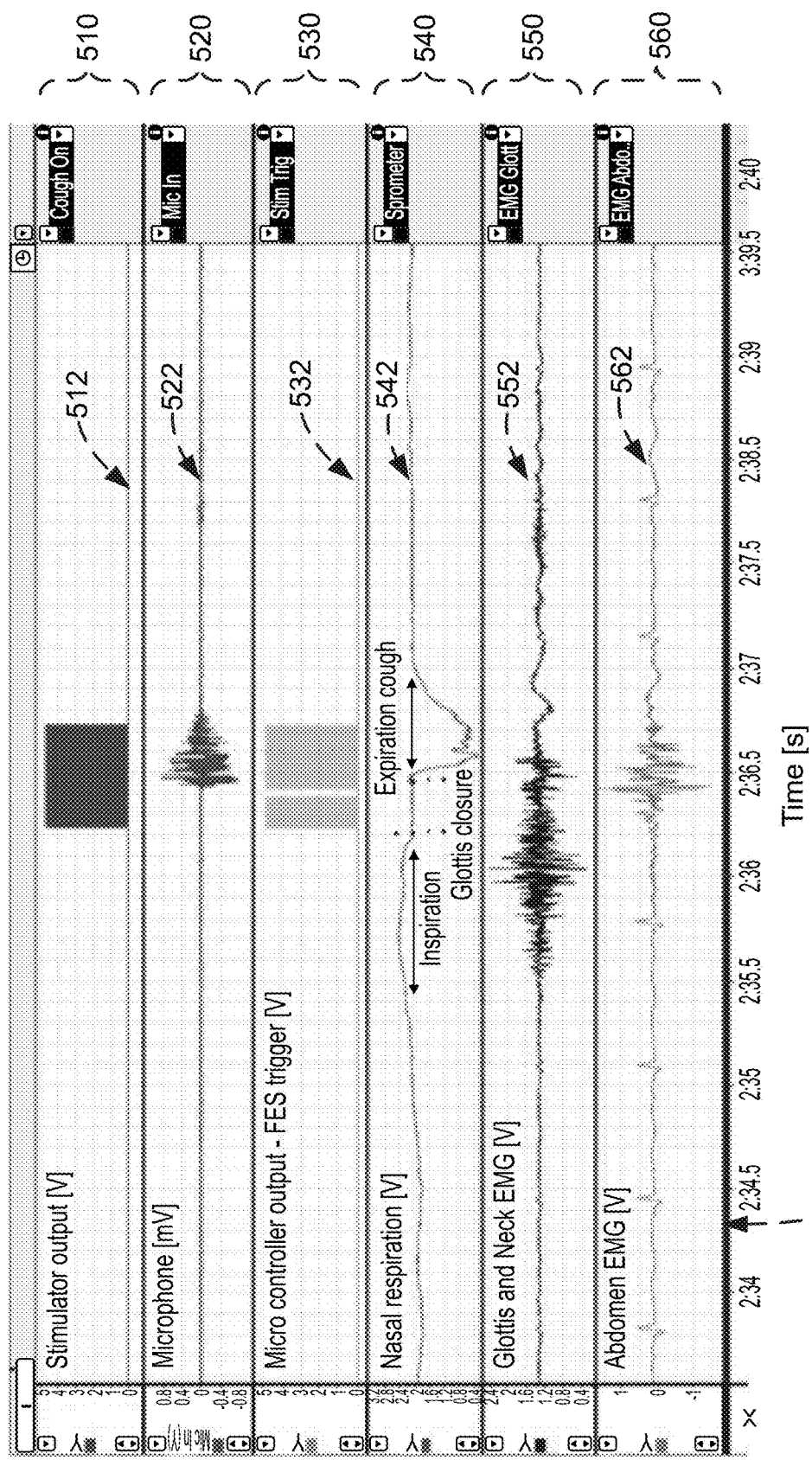
FIG. 5 depicts six graphs showing a stimulator signal, a microphone signal, a FES trigger signal, a nasal flow signal, a glottis and neck EMG signal and an abdomen EMG signal as measured by a system such as the system of FIG. 4 on a non-paralyzed subject.
Figure 7:
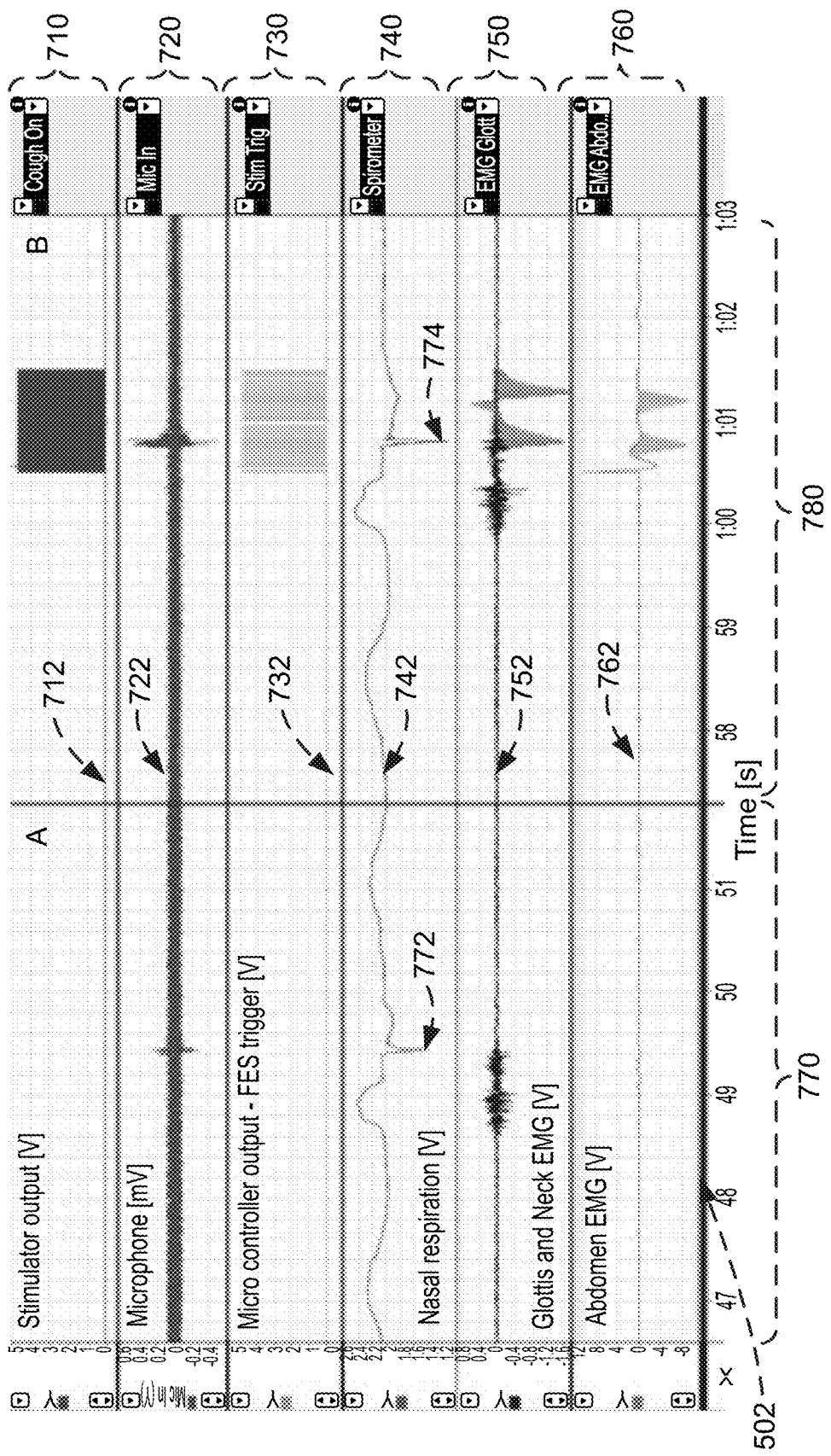
FIG. 7 depicts six graphs showing a stimulator signal, a microphone signal, a FES trigger signal, a nasal flow signal, a glottis and neck EMG signal and an abdomen EMG signal as measured by a system such as the system of FIG. 4 on a subject with tetraplegia, without stimulation and with stimulation delivered by two electrode pairs as illustrated in FIG. 6A.
Figure 8:
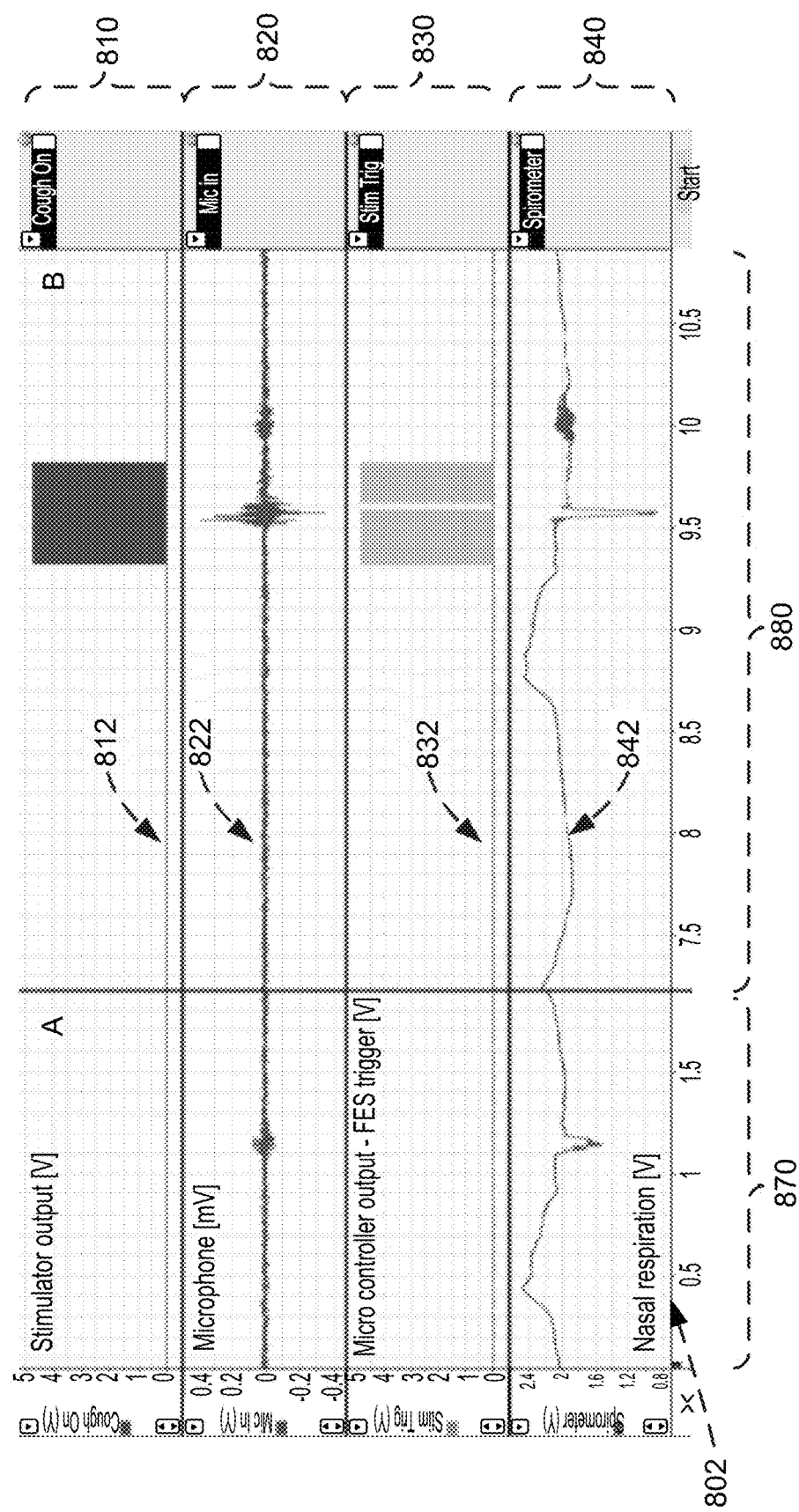
FIG. 8 depicts four graphs showing a stimulator signal, a microphone signal, a FES trigger signal and a nasal flow signal as measured by a system such as the system of FIG. 4 on a subject with tetraplegia, without stimulation and with stimulation delivered by four electrode pairs as illustrated in FIG. 6B.

The nasal air flow 222 in the middle graph 220 depicts a nasal air flow trace and the lower graph 230 depicts EMG activity. It is noted that in the present application some of the Figures showing nasal air flow traces, such as the middle graph 220, show expiration as a trace toward a top of the graph, while some of the Figures, such as FIGS. 5, 7 and 8, show expiration as a trace toward a bottom of the graph. A person skilled in the art can differentiate between the two types of traces based on the direction of sections indicates as expiration, inspiration, and expiration cough.

It is noted that in the nasal air flow 222 trace, point 226 is considered by the inventors to potentially indicate glottis closure.

It is noted that increased EMG activity 234 is depicted in the lower graph 230 at approximately the same time as glottis closure in the middle graph 220.

It is noted that in many cases, different time intervals were measured between the EMG activity and a beginning 226 of the plateau in the nasal air flow 222.

To further aid discovery of nasal breathing parameters during coughing an endoscopic video camera was added (not shown in FIG. 1), synchronized with the nasal air flow 222 measurements, the microphone signal 212 and the EMG signal 232 during coughing.

The addition of the endoscopic video camera provided a reproducible time difference measurement between glottis closure and the nasal respiration plateau.

7 non-paralyzed subjects were measured using the set-up including the endoscopic video camera, and the time difference between the glottis closure onset, observed by video, and the beginning of the plateau was measured at 38±10 milliseconds (as further described below with reference to FIG. 3).

Figure 3:
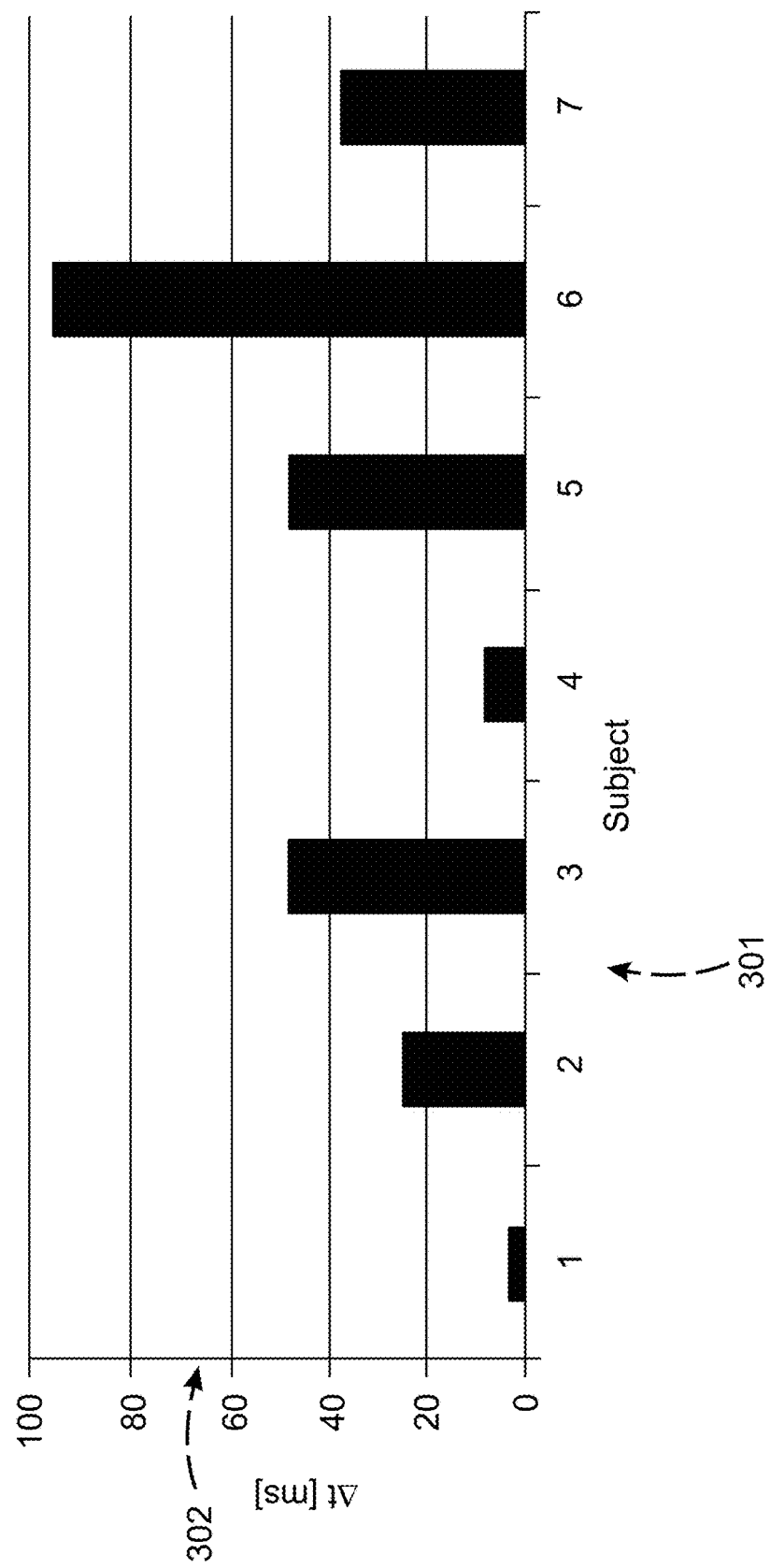
FIG. 3 is a bar graph of a time difference between a beginning of a plateau in nasal air flow and glottis closure onset as observed by video.

Reference is now made to FIG. 3, which is a bar graph of a time difference between a beginning of a plateau in nasal air flow and glottis closure onset as observed by video.

FIG. 3 depicts an X-axis 301 indexing 7 of the above 7 non-paralyzed subjects, and a Y-axis 302 showing the time difference between the beginning of the plateau in nasal air flow and glottis closure onset as observed by video for the 7 subjects.

Furthermore, a mean closure time of the glottis was found to be approximately 200 milliseconds. The mean closure time of the glottis is also supported by scientific literature, which supports the findings.

In some embodiments, a beginning of the plateau after a sharp drop in inspiration air flow, as depicted in FIG. 2, is taken as a moment of closure of the glottis.

In some embodiments, the FES is activated exactly at the beginning of the glottis closure.

In some embodiments, software for detection of a respiratory feature which indicates glottis closure was developed, which continuously samples a nasal air flow trace. A trigger for providing the FES is optionally activated when the software detects two consecutive features in the nasal air trace. A first feature is an existence of a flat interval lasting approximately 50 ms.—a plateau—and a second feature is a negative slope in the preceding 50 ms.

In some embodiments, the 50 ms flat interval (plateau) is optionally detected by calculating a difference between a maximum and a minimum nasal air flow trace values over a sample interval. The difference is sampled at short intervals and a 'plateau' is detected if the difference is smaller than a specific threshold. In some embodiments, all samples have to be within a specified window from a baseline. In some embodiments the sampling rate of the difference is 1 kHz. In some embodiments the sampling rate ranges from 100 Hz to 10 kHz.

In some embodiments, to detect the slope, a straight line is calculated based on the first and the last samples of a slope test interval and a set of residual values is produced by subtracting the sampled signals from the straight line. A slope is considered detected if a difference between a maximum residual value and a minimum residual value is smaller than a corresponding threshold.

In some cases the slope was detected too often, producing false-alarms, and in such cases cough determination was not successful.

In some embodiments, to compensate for false-alarms and to potentially improve cough determination, a second method is used. In the second method, both the flat interval (plateau) and slope interval were each fitted to a straight line and two coefficients ($\alpha$ and $\beta$) were extracted using the following equations:

$$\hat{\beta} = \frac{\sum_{i=1}^{n}(x_i - \bar{x})(y_i - \bar{y})}{\sum_{i=1}^{n}(x_i - \bar{x})^2} = \frac{\sum_{i=1}^{n}x_i y_i - \frac{1}{n}\sum_{i=1}^{n}x_i \sum_{j=1}^{n}y_j}{\sum_{i=1}^{n}(x_i^2) - \frac{1}{n}\left(\sum_{i=1}^{n}x_i\right)^2} =$$

$$\frac{\overline{xy} - \bar{x}\bar{y}}{\overline{x^2} - \bar{x}^2} = \frac{\text{Cov}[x, y]}{\text{Var}[x]} = r_{xy}\frac{s_y}{s_x}, \hat{\alpha} = \bar{y} - \hat{\beta}\bar{x},$$

Note: In the above equation, $r_{xy}$ is a sample correlation coefficient between x and y, $s_x$ is a standard deviation of x, and $s_y$ is correspondingly the standard deviation of y, and a horizontal bar over a variable means a sample average of that variable:

$$\overline{xy} = \frac{1}{n}\sum_{i=1}^{n}x_i y_i.$$

In some embodiments the FES is triggered if the $\alpha$ and the $\beta$ coefficients, obtained from the equation above, are below a certain threshold.

An Example Nasal Airflow and FES System

An example embodiment of a system combining nasal air flow analysis and FES was tested on 10 non-paralyzed subjects. The subjects were asked to breathe normally through the mouth and to cough voluntarily, and the ability of the system to synchronize cough determination and FES activation at the time frame of coughing was tested.

The example embodiment system included:
Nasal respiratory measurements.
EMG recording of glottis and other neck muscles activity.
EMG recording of abdominal muscles activity.
Recording of trigger output of our device.
Recording of stimulator output.
Sound recording.

Figure 4:
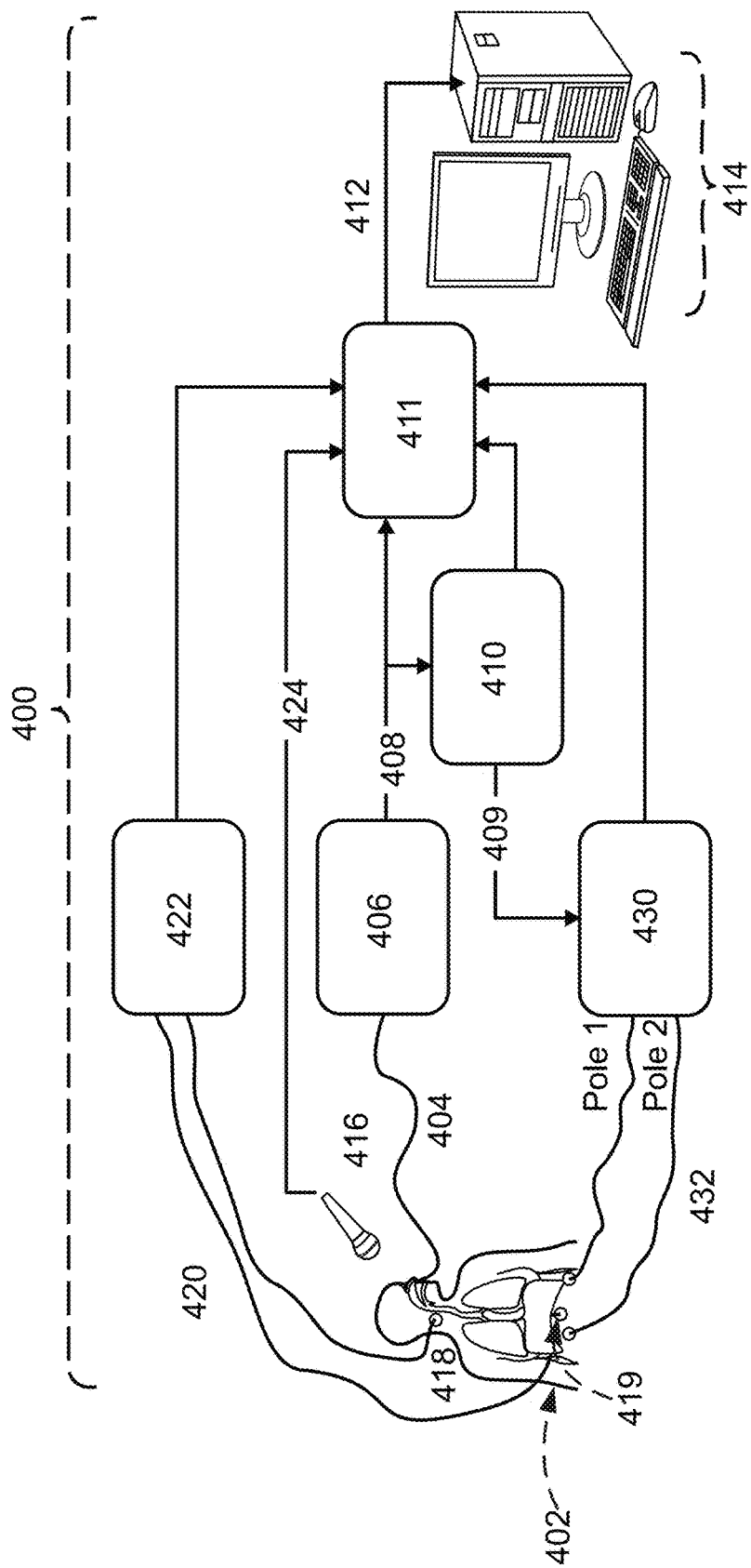
FIG. 4 is a simplified illustration of a system for assisting coughing according to an example embodiment of the invention.

Reference is now made to FIG. 4, which is a simplified illustration of a system 400 for assisting coughing according to an example embodiment of the invention.

FIG. 1 depicts a patient 402 with a cannula 404 for providing nasal air to one or more sensors 406. In some embodiments the sensors 406 optionally sense nasal air flow.

In some embodiments the sensors 406 optionally sense air pressure.

The sensors 406 provide an output signal 408, which in some embodiments—as described above with reference to the Arduino microcontroller—may be analog, and in some embodiments may be digital.

In some embodiments the output signal 408 is optionally provided to a microcontroller 410, such as the above-mentioned Arduino, and/or to a laboratory instrumentation unit 411 such as an AD Instruments Power Lab unit.

In some embodiments the laboratory instrumentation unit 411 optionally provides output signals 412 to a computer 414, optionally for further processing and/or storage.

In some embodiments the laboratory instrumentation unit 411 optionally accepts input from additional sources of signals which may optionally also serve, alone or in combination with each other and/or with the nasal air signals, to determine an oncoming cough or a patient command.

In some embodiments a microphone 416 optionally provides an input signal to the laboratory instrumentation unit 411.

In some embodiments one or more electromyography (EMG) throat electrodes 418 are optionally connected to the patient's 402 throat, and provide signals 420 to an optional electrophysiological signal amplifier 422, which optionally provides an output 424 to the laboratory instrumentation unit 411.

In some embodiments one or more electromyography (EMG) abdominal electrodes 419 are optionally connected to the patient's 402 body, and optionally provide signals 420 to an optional electrophysiological signal amplifier 422, which optionally provides an output 424 to the laboratory instrumentation unit 411.

FIG. 4 depicts the microcontroller 410 providing an output signal 409, optionally to a FES controller 430, such as an instruction to the FES controller 430 to generate one or more electric stimulation signals to electric stimulation electrodes 432 attached to the body of the patient 402.

In FIG. 4, by way of a non-limiting example, output of the controller 430 comprises of two leads: Pole1 and Pole2.

In some embodiments the FES controller 430 provides the same electric stimulation signals in parallel over any number of electrodes, such as one electrode pair, two electrode pairs, three electrode pairs, four electrode pairs, and more electrode pairs.

In some embodiments (not shown) the electrodes 420 optionally collect EMG signals from the abdomen, and provide the EMG signals (not shown) to the electrophysiological signal amplifier 422 or to a separate electrophysiological signal amplifier (not shown), either of which optionally provide an output which may optionally be gathered by the computer 414 as described above with reference to the throat EMG signals 418.

It is noted that nasal respiration may be specific, per each individual, and dynamics of the soft palate (glottis) may change during measurements.

In some embodiments the nasal air flow analysis and FES system continuously measures the nasal air flow during coughing, optionally distinguishes between coughing and normal breathing, and activates the FES at an exact timing of glottis closure, as shown FIG. 5 and described below.

Reference is now made to FIG. 5, which depicts six graphs 510 520 530 540 550 560 showing a stimulator signal 512, a microphone signal 522, a FES trigger signal 532, a nasal flow signal 542, a glottis and neck EMG signal 552 and an abdomen EMG signal 562 as measured by a system such as the system 400 of FIG. 4 on a non-paralyzed subject.

FIG. 5 depicts six graphs 510 520 530 540 550 560 share a common X-axis 502 depicting time.

It is noted that low values of the nasal flow signal 542 correspond to expiration, while high values of the nasal flow signal 542 correspond to inspiration.

It is noted that neck muscle activity, as depicted by the glottis and neck EMG signal 552, starts earlier than glottis closure, as depicted in the nasal flow signal 542. In the example depicted in FIG. 5, the neck muscle activity starts earlier than glottis closure by 421±181 milliseconds.

It is noted that abdominal muscle activity as depicted by the abdomen EMG signal 562 starts later than neck muscle activity as depicted by the glottis and neck EMG signal 552, and occurs earlier than glottis closure by 182±163 milliseconds.

The above results indicate that neck muscles contract during inspiration, possibly especially when deep inhalation is followed by a cough. In addition it is noted that an inhalation before a cough is typically larger in most cases than a non-cough inhalation, and that the ratio between a maximum of a cough-related inhalation and a previous, non-cough-related inhalation is 1.09±0.06. Typically, a cough is characterized by a large inspiratory nasal air flow peak.

During course of producing the results depicted in FIG. 5, when cough was determined, the microcontroller 410 provided the FES controller 430 with an output signal 409, by way of a non-limiting example with a pulse signal trigger at a frequency of 100 Hz for 500 ms, within a response time of 37±12 milliseconds.

The FES controller 430 produced a stimulator output as shown by the stimulator signal 512 in FIG. 5.

In some embodiments, the FES is applied for 500 ms, as described above, in some embodiments, a shorter FES signal is applied, for example 250 ms, and in some examples a longer FSE signal is applied, for example 1000 ms, or even 1250 ms.

It is noted that in the non-paralyzed subjects the stimulation was correctly synchronized with normal abdominal muscle activity. In most cases normal abdominal muscle activity started earlier by 100±130 milliseconds.

It is noted that stimulation can optionally be delivered at normal abdominal muscle activity timing for coughing for people with tetraplegia.

The system 400 of FIG. 4 was tested on a person with tetraplegia. Stimulation was delivered directly to the abdominal muscles using self-adhesive surface electrodes.

Figure 6C:
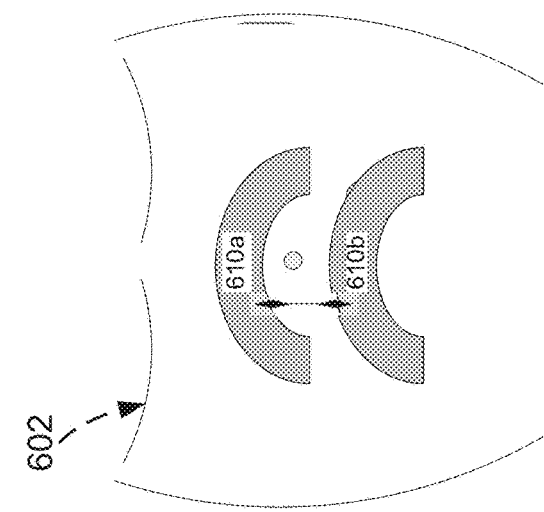
FIGS. 6A, 6B and 6C are simplified illustrations of stimulation electrode arrangements on an abdomen of a subject according to example embodiments of the invention.
Figure 6B:
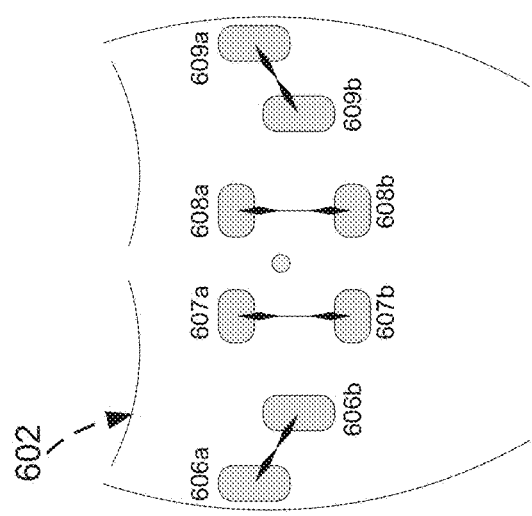
Figure 6A:
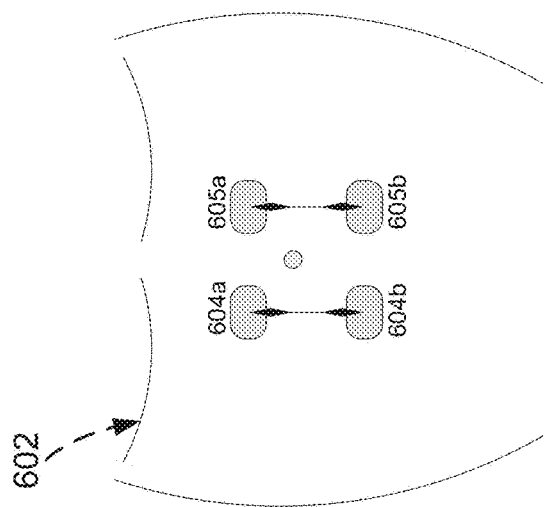

Reference is now made to FIGS. 6A, 6B and 6C which are simplified illustrations of stimulation electrode arrangements on an abdomen 602 of a subject according to example embodiments of the invention.

FIGS. 6A, 6B and 6C depict a simplified outline 602 indicating a general shape of a subject's abdomen, and a navel represented by a circle near the middle of the outline 602.

FIG. 6A depicts a non-limiting example embodiment with two electrode pairs 604*a* 604*b* 605*a* 605*b* arranged on the abdomen 602 of the subject. The first electrode pair 604*a* 604*b* optionally has two poles, and the second electrode pair 605*a* 605*b* optionally has two poles.

In some embodiments the two separate electrode-pairs 604*a* 604*b* and 605*a* 605*b* are stimulated by two separate stimulation signals.

In some embodiments the two separate electrode-pairs 604*a* 604*b* and 605*a* 605*b* are stimulated in parallel by one stimulation signal, as during a first test described below.

During a first test, stimulation was delivered by the FES controller 430 with one output channel feeding two separate electrode-pairs 604*a* 604*b* and 605*a* 605*b* in parallel, for a total of four electrodes arranged as illustrated in FIG. 6A.

FIG. 6B depicts a non-limiting example embodiment with four electrode pairs 606*a* 606*b* 607*a* 607*b* 608*a* 608*b* 609*a* 609*b* arranged in four separate electrode-pairs on the abdomen 602 of the subject.

In some embodiments the four separate electrode-pairs 606*a* 606*b* 607*a* 607*b* 608*a* 608*b* 609*a* 609*b* are stimulated by four (or less) separate stimulation signals.

In some embodiments the four separate electrode-pairs 606a 606b 607a 607b 608a 608b 609a 609b are stimulated by one stimulation signal, as during a second test described below.

During a second test a four separate electrode-pair configuration was tested, for a total of eight electrodes 606a 606b 607a 607b 608a 608b 609a 609b arranged in pairs, as illustrated in FIG. 6B. Abdominal muscles were stimulated bilaterally, with two electrode pairs stimulating the rectus muscles of the abdomen, and two electrode pairs stimulating the lateral abdominal muscle group, that is the transverse muscles of abdomen, and abdominal external and internal muscles.

In some embodiments the electrode pairs are used with a first electrode of a pair being a positive electrode and a second electrode of the pair being a negative electrode.

FIG. 6C depicts a non-limiting example embodiment with two area electrodes 610a 610b arranged as an electrode-pair on the abdomen 602 of the subject.

In some embodiments the two area electrodes 610a 610b are stimulated by one stimulation signal.

In some embodiments only one FES output channel is used. The one output channel may optionally be connected to all pairs of electrodes. In this configuration the FES system was found to be highly effective in eliciting cough.

In some embodiments, the electrodes are implanted rather than attached to a patient's skin.

In some embodiments an external connection to the electrodes is provided to power the implanted electrodes.

In some embodiments power is provided to the electrodes through the skin, optionally by a contactless inductive power supply.

FIG. 7 and FIG. 8 below depict additional results of using the system of FIG. 4, and demonstrate eliciting a highly effective cough.

Reference is now made to FIG. 7, which depicts six graphs 710 720 730 740 750 760 showing a stimulator signal 712, a microphone signal 722, a FES trigger signal 732, a nasal flow signal 742, a glottis and neck EMG signal 752 and an abdomen EMG signal 762 as measured by a system such as the system 400 of FIG. 4 on a subject with tetraplegia, without stimulation 770 and with stimulation 780 delivered by two electrode pairs as illustrated in FIG. 6A.

The six graphs 710 720 730 740 750 760 share a common X-axis 702 depicting time.

It is noted that low values of the nasal flow signal 742 correspond to expiration, while high values of the nasal flow signal 742 correspond to inspiration.

It is noted that comparing coughing characteristics during natural cough (without stimulation 770), vs. a stimulated cough (with stimulation 780) shows:

(1) higher abdominal muscle activity during a stimulated cough;

(2) stimulation produced a stronger cough, confirmed by a measured sound intensity as depicted by the microphone signal 722, and by a ratio between an expiration depth 772 of a non-stimulated cough and an expiration depth 774 of a stimulated cough, as depicted by the nasal flow signal 742.

Reference is now made to FIG. 8, which depicts four graphs 810 820 830 840 showing a stimulator signal 812, a microphone signal 822, a FES trigger signal 832 and a nasal flow signal 842 as measured by a system such as the system 400 of FIG. 4 on a subject with tetraplegia, without stimulation 870 and with stimulation 880 delivered by four electrode pairs as illustrated in FIG. 6B.

The four graphs 810 820 830 840 share a common X-axis 802 depicting time.

It is noted that low values of the nasal flow signal 842 correspond to expiration, while high values of the nasal flow signal 842 correspond to inspiration.

With reference to the test of the system of FIG. 4, effectiveness of the stimulated cough was also assessed quantitatively by measuring a total volume of expiration after a natural cough, approximately 1 liter, and after a stimulated cough, approximately 3 liters.

In some embodiments parameters of the FES signal are optionally varied.

In some embodiments, FES is delivered for a period of 1 second to two electrode pairs, at a frequency of 50 Hz, a constant current of 100 mA per electrode pair, and at a 200 µs pulse duration. A subject to which the above FES was applied reported that it was hard for him to inhale after the stimulation.

In some embodiments, FES is delivered for a period of 0.5 second to four electrode pairs, at a frequency of 100 Hz, a constant current of 250 mA for the four electrode pairs (62.5 mA per electrode pair), and at a 200 µs pulse duration (as depicted in FIG. 8 above). The subject to which the above FES was applied reported that the stimulated cough was effective and did not cause any discomfort.

In such embodiments, in contrast with the above-mentioned article by Gollee H et al., titled "A control system for automatic electrical stimulation of abdominal muscles to assist respiratory function in tetraplegia", determination of when to apply stimulation is measured by nasal air flow parameters rather than mouth air parameters; a trigger point is identified differently, optionally timed to glottis closure, optionally using the method described above; and the period of application of stimulation is shorter.

Determining when to Start Providing FES

In some embodiments, signal analysis is applied to the nasal air flow signal (such as the nasal flow signal 742 of FIG. 7 and the nasal flow signal 842 of FIG. 8). The signal analysis optionally assists detecting when a patient intends to cough, and/or when to apply FES to assist the cough.

The signal analysis optionally detects parameters which relate to breathing and coughing.

Some non-limiting example parameters include:

determining a slope of flow of inspiration data points, which corresponds to an intensity of air flow;

determining a value of minimum flow following inspiration, which corresponds to glottis closure; and determining a duration of minimum flow following inspiration, which corresponds to a duration of glottis closure.

In some embodiments, a baseline of normal breathing is established using typical and/or average values and optionally measured deviations from the average values for a specific patient.

In some embodiments, a study of breathing cycles which include coughing is established using typical and/or average values and optionally measured deviations from the average values for a specific patient.

In some embodiments, the above parameter values are optionally collected for several normal breathing cycles, and/or optionally collected for several breathing cycles which include a cough, whether natural or FES-induced.

In some embodiments a difference between parameters typical for normal breathing and parameters for breathing which includes a cough optionally serve an automatic system to detect when a patient intends to cough, by analyzing the patient's breathing pattern.

The inventors have performed studies of glottis closure duration prior to a cough, and have measured a range of glottis closure durations from approximately 200 milliseconds to approximately 300 milliseconds.

The inventors have discovered that good coughing occurs when FES starts somewhat prior to the end of the period of glottis closure, for example approximately 30 milliseconds prior to the end of the period of glottis closure.

In some embodiments, FES is caused to start in a range of 20-100 milliseconds prior to the end of the period of glottis closure.

In some embodiments, when a patient's typical or average glottis closure duration is known, FES is caused to start in a range of 10%-30% of the patient's glottis closure duration prior to the end of the period of glottis closure.

In some embodiments, the glottis closure duration is measured per individual patient so that starting FES prior to end of glottis closure not accidentally start after end of glottis closure because of a large difference, for example in a range of 100-300 milliseconds, of glottis closure durations between patients.

It is noted that good coughing is optionally determined by one or more of: a patient's providing a subjective assessment; a measure of air flow volume expired in a cough; and a measure of air flow velocity during a cough.

In some embodiments, a training period is set up, where a patient coughs several times, e.g. 3 times or more, and an average duration of glottis closure is calculated for the patient. Based on the average duration of glottis closure during the training period, a system optionally detects beginning of glottis closure, as described elsewhere herein, and starts FES prior to the end of the average period of glottis closure, for example approximately 30 milliseconds prior to the end of the average period of glottis closure.

In some embodiments, a training period is set up, where a patient coughs several times, e.g. 3 times or more, and an average of several parameters are measured off the air flow signal. The following non-limiting example parameters are optionally measured and optionally averaged:

a maximum of inspiration;

a value of a slope of inspiration air flow for instances where the inspiration air flow is followed by minimum in air flow; and a duration of glottis closure.

In some embodiments, the average values of the maximum of inspiration and of the value of the slope of inspiration air flow are optionally taken as representative of a patient's intent to cough. When values within a threshold difference from the average are measured for the patient, the cough assisting system optionally detects intent to cough.

In some embodiments, the average value of the duration of the glottis closure in the patient are optionally used to determine when to apply FES to the patient.

In some embodiments, FES is optionally applied prior to an expected end of glottis closure, optionally based on the average value of the duration of the glottis closure in the patient.

In some embodiments, training is performed continuously, and when a patient coughs an average duration of glottis closure is optionally adjusted to be a running average or an average of last N coughs.

In some embodiments, a beginning time of glottis closure is detected or estimated when the nasal flow signal has a negative slope followed by an end of the negative slope at a minimum value. The beginning time of glottis closure is optionally estimated as the time of reaching the minimum.

In some embodiments, the time for starting to provide FES is determined relative to the detected beginning time of glottis closure.

In some embodiments, the time for starting to provide FES is determined relative to the detected beginning time of glottis closure, plus a determined average period of glottis closure for a patient.

Optimizing when to Start Providing FES

In some embodiments, the time when to start FES is optionally adjusted for improving, or optimizing, beneficent effect on a patient. The optimization optionally occurs by adjusting when to start providing FES relative to a specific point in time.

In some embodiments the time when to start FES is optionally adjusted by a user, such as the patient or a medical practitioner, providing adjust instructions such as "earlier" or "later", or by the user actually adjusting a number via numeric input or by rotating a knob or moving a real or virtual slider in a user interface.

In some embodiments the specific point in time is the time determined for the patient's glottis closure. In some embodiments the specific point in time is the time determined for the patient's glottis closure plus an average duration of the patient's glottis closure over a plurality of coughs. In some embodiments the specific point in time is the time when the patient activates a request signal for providing the FES.

In some embodiments adjusting when to start providing FES is performed by using machine learning to learn at what time starting to provide FES provides most benefit to the patient. On some embodiments providing most benefit is optionally determined by measuring an output parameter based on a cough befitting from the FES, and optionally affecting the output parameter by adjusting when to start providing FES, optionally relative to the above-mentioned specific point in time.

Following are non-limiting examples of output parameters which are measured, each separately or in combination, and optionally used to adjust when to start providing FES:

a value of a patient's feedback;

a professional, such as a medical practitioner, providing a feedback value;

a value of a physiological parameter measured off the patient with a relation to breathing and/or coughing, such as air flow temperature, $CO_2$ concentration (Capnography), electromyography (EMG);

a value of a measurable parameter such as PEF (Peak Expiratory Flow);

a value of a measurable parameter such as maximum nasal expiration during a cough;

a value of a measurable parameter such as maximum volume of a sound of a cough, optionally as measured by a microphone; and a value of a measurable parameter such as maximum output of lung air, optionally by coughing into a measuring device during training of a system providing FES.

Optimizing Duration of FES

In some embodiments, methods similar to the methods described above for adjusting and/or optimizing the time when to start Functional Electrical Stimulation (FES) of abdominal muscles are used to adjust and/or optimize duration of the FES.

In some embodiments, the duration of the FES is optionally adjusted for improving, or optimizing, beneficent effect on a patient. The optimization optionally occurs by adjusting the duration of the FES.

In some embodiments the duration of the FES is a fixed duration.

In some embodiments the duration of the FES is adjusted by a user, such as the patient or a medical practitioner, providing adjust instructions such as "longer" or "shorter", or by the user actually adjusting a number via numeric input or by rotating a knob or moving a real or virtual slider in a user interface.

In some embodiments adjusting the duration of the FES is performed by using machine learning to learn what the duration of the FES provides most benefit to the patient. On some embodiments providing most benefit is optionally determined by measuring an output parameter based on a cough befitting from the FES, and optionally affecting the output parameter by adjusting the duration of the FES.

Following are non-limiting examples of output parameters which are measured, each separately or in combination, and optionally used to adjust the duration of the FES:

a value of a patient's feedback;

a professional, such as a medical practitioner, providing a feedback value;

a value of a physiological parameter measured off the patient with a relation to breathing and/or coughing, such as air flow temperature, $CO_2$ concentration (Capnography), electromyography (EMG);

a value of a measurable parameter such as PEF (Peak Expiratory Flow);

a value of a measurable parameter such as maximum nasal expiration during a cough;

a value of a measurable parameter such as maximum volume of a sound of a cough, optionally as measured by a microphone; and a value of a measurable parameter such as maximum output of lung air, optionally by coughing into a measuring device during training of a system providing FES.

Additional Example Nasal Airflow and FES Embodiments

Figure 9A:
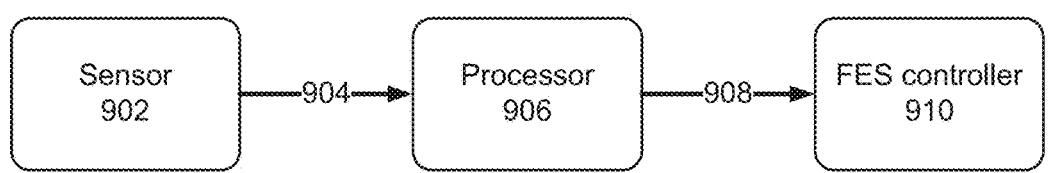
FIG. 9A is a simplified block diagram illustration of a system for assisted coughing according to an example embodiment of the invention.

Reference is now made to FIG. 9A, which is a simplified block diagram illustration of a system 900 for assisted coughing according to an example embodiment of the invention.

FIG. 9A depicts:

a first sensor 902 for measuring a parameter which can indicate a closed glottis and producing a first output signal 904;

a processor 906 for receiving the first output signal 904, determining the closed glottis and generating an instruction 908 for a Functional Electric Stimulation (FES) controller 910 based, at least in part, on the determining; and the FES controller 910 configured for generating an electric stimulation signal.

In some embodiments, the first sensor of FIG. 9A is a nasal air sensor configured for sensing the patient's nasal air flow.

Figure 9B:
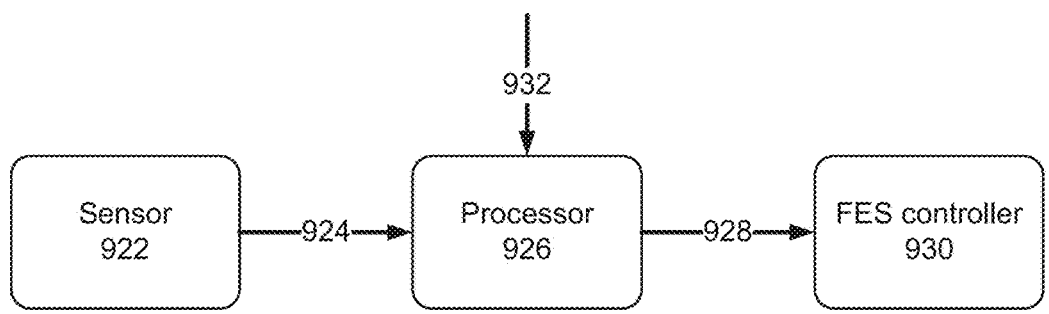
FIG. 9B is a simplified block diagram illustration of a system for assisted coughing according to an example embodiment of the invention.

Reference is now made to FIG. 9B, which is a simplified block diagram illustration of a system 920 for assisted coughing according to an example embodiment of the invention.

FIG. 9B depicts:

a first sensor 922 for measuring a parameter which can indicate a closed glottis and producing a first output signal 924;

a processor 926 for receiving the first output signal 924, a command input 932, determining the closed glottis and generating an instruction 928 for a Functional Electric Stimulation (FES) controller 930 based, at least in part, on the determining; and the FES controller 930 configured for generating an electric stimulation signal.

In some embodiments, the first sensor of FIG. 9B is a nasal air sensor configured for sensing the patient's nasal air flow.

In some embodiments, the command input of FIG. 9B is provided by a second sensor configured to accept the command input.

The second sensor may even be a button or similar actuator for enabling the determining of the closed glottis, so that potentially cough stimulation is not stimulated unless something or someone provides a command allowing such stimulation.

In some embodiments, the second sensor is configured to accept the command input from a caregiver.

In some embodiments, the second sensor is configured to accept the command input from a patient.

In some embodiments, the second sensor is configured to accept the command input from a computer, optionally configured to stimulate assisted coughing according to some criterion, such as every period of time, or according to a sound of a patient breathing, such as a sound of loud breathing.

In some embodiments the patient command input is provided via the same nasal air flow sensor which is the first sensor.

In some embodiments the second sensor is optionally one or more of:

an eye blink sensor;

a microphone;

an electromyography (EMG) electrode configured for sensing the patient's EMG activity of the neck muscles;

a chest belt for monitoring respiration; and an electrophysiological sensor for sensing abdominal muscles, optionally designed to sense an attempt at coughing by a patient, optionally providing a command enabling stimulated coughing upon a subsequent attempt at coughing by the patient.

Figure 10A:
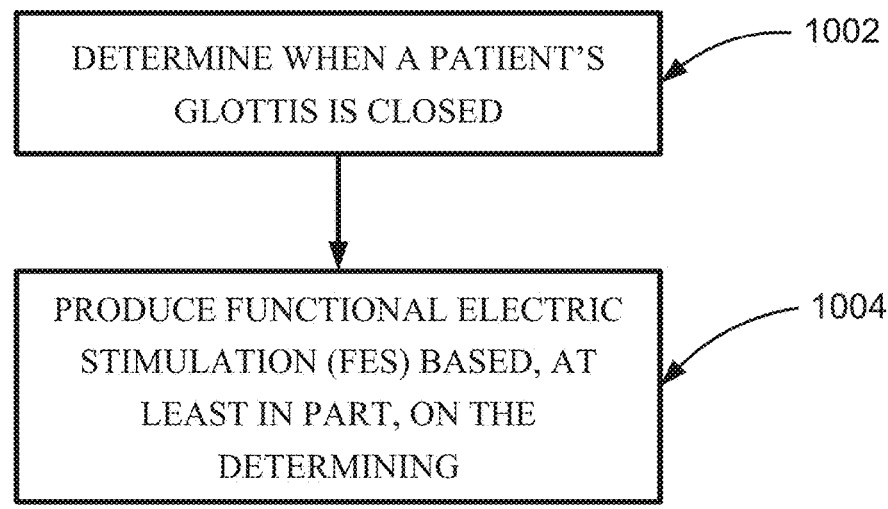
FIG. 10A is a simplified flow chart diagram of a method for assisted coughing according to an example embodiment of the invention.

Reference is now made to FIG. 10A, which is a simplified flow chart diagram of a method for assisted coughing according to an example embodiment of the invention.

FIG. 10A depicts a method including:

determining when a patient's glottis is closed (1002); and producing Functional Electric Stimulation (FES) based, at least in part, on the determining (1004).

Figure 10B:
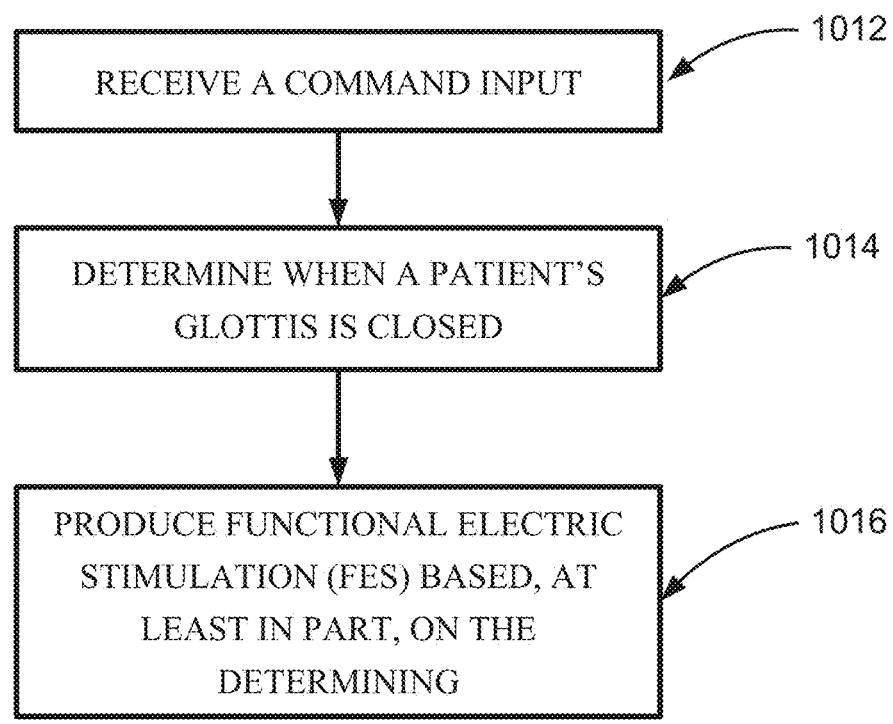
FIG. 10B is a simplified flow chart diagram of a method for assisted coughing according to another example embodiment of the invention.

Reference is now made to FIG. 10B, which is a simplified flow chart diagram of a method for assisted coughing according to another example embodiment of the invention.

FIG. 10B depicts a method including:

receiving a command input (1012);

determining when a patient's glottis is closed (1014); and producing Functional Electric Stimulation (FES) based, at least in part, on the determining (1016).

In some embodiments the receiving of the command input includes receiving the command input from a processor analyzing a signal from a sensor configured to sense receipt of a command input from the patient.

In some embodiments the receiving of the command input includes receiving the command input from a processor analyzing a nasal air signal from a patient's nasal air flow sensor.

In some embodiments the receiving of the command input includes receiving the command input from a processor receiving input from one or more of:

an eye blink sensor;

a microphone;

an electromyography (EMG) electrode configured for sensing the patient's EMG activity of the neck muscles; and an electrophysiological sensor for sensing abdominal muscles.

In some embodiments the receiving of the command input includes receiving the command input from a caregiver, possibly by the caregiver providing an input to a computerized system, and/or even by the caregiver pressing a button.

Smart Coughing Assistance

In some embodiments, some parameters used by a system for assisted coughing are optionally set by a user. Some non-limiting examples of such parameters will be listed below.

In some embodiments, a caregiver, such as a nurse or a physician, optionally sets the parameters.

In some embodiments, a patient optionally sets the parameters.

In some embodiments, especially when the patient is limited in movement and/or muscle control, a method for input from the patient may optionally be based upon the method described in above-mentioned PCT Patent Application WO 2010/122560 of Sobel et al, which describes a method of receiving input from a user, comprising measuring a nasal air parameter and generating an instruction for one or both of a device and controller based on said measurement.

In some embodiments setting the parameters is performed by navigating a menu system, optionally using the system of described in above-mentioned PCT Patent Application WO 2010/122560 of Sobel et al.

In some embodiments setting the parameters is performed by direct input of a set of commands, without navigating a menu.

A non-limiting list of adjustable parameters assisting coughing includes:

(a) setting an earlier or later onset of FES relative to determination of onset of glottis closure;

(b) setting a longer or shorter duration of FES to abdominal muscles;

(c) setting higher or lower voltage in an FES electric signal;

(d) setting duration of a window of time during which system seeks to detect onset of glottis closure in order to assist coughing; and (e) setting a desired coughing regime, such as a specific times per hour, appropriate for a patient, optionally according to a specific medical condition.

Some aspects of smart coughing assistance include embodiments which monitor a patient's breathing, optionally detecting sonorous respiration, and providing automatic coughing assistance.

Some aspects of smart coughing assistance include embodiments which monitor a patient's breathing, optionally detecting sonorous respiration, and providing feedback to a patient and/or a caregiver that coughing assistance may be desirable.

Some aspects of smart coughing assistance include embodiments which maintain a specific regime of coughing, such as setting a number of coughs per unit of time. The coughs may be automatically generated and/or suggested to a patient and/or caregiver by providing an alert.

Figure 10C:
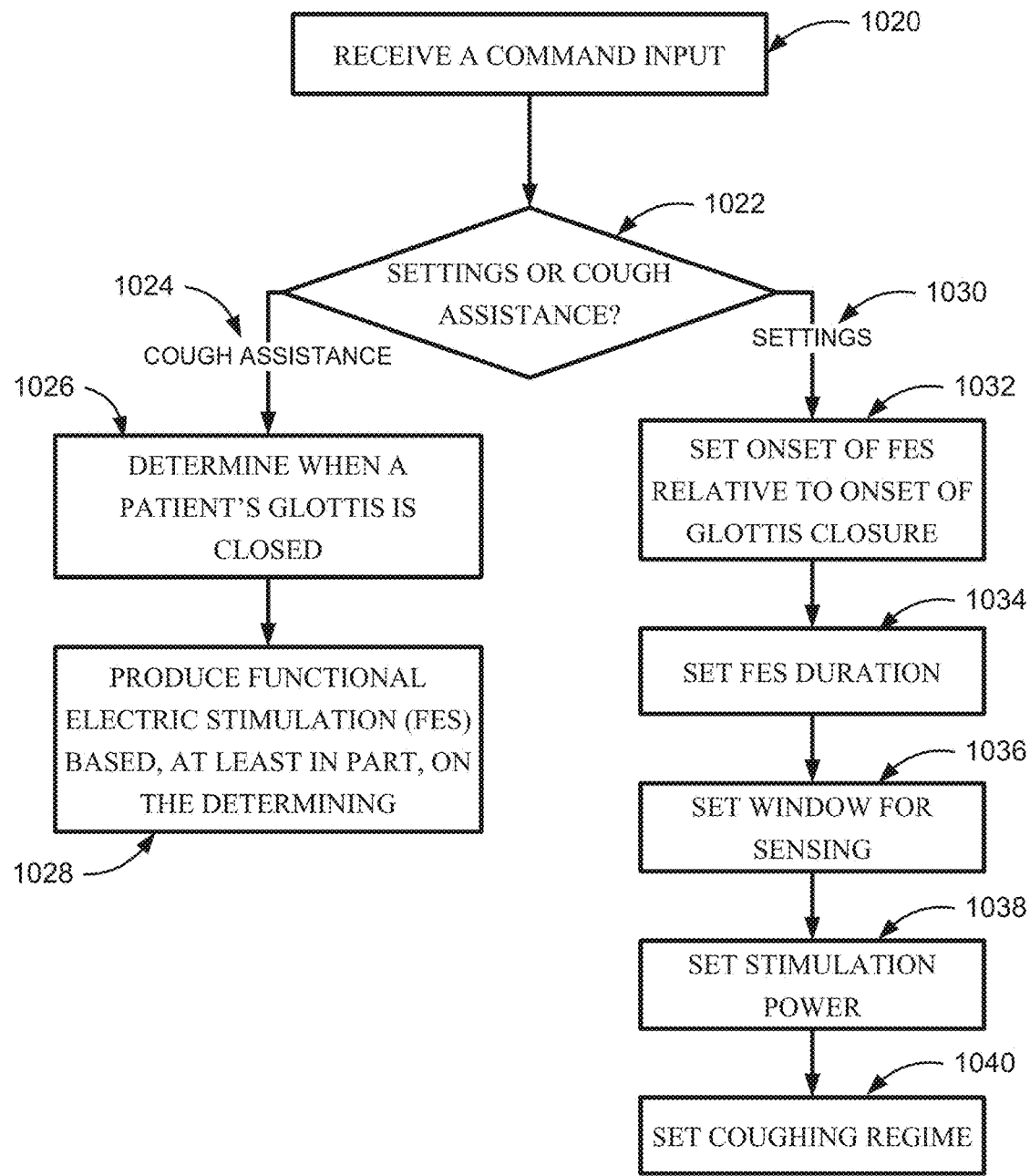
FIG. 10C is a simplified flow chart diagram of a method for assisted coughing according to yet another example embodiment of the invention.

Reference is now made to FIG. 10C, which is a simplified flow chart diagram of a method for assisted coughing according to yet another example embodiment of the invention.

FIG. 10C depicts a method including:
receiving a command input (1020);
determining whether the command input corresponds to a command for cough assistance or a command to set parameters in a cough assistance system (1022);
if the command input corresponds to a command for cough assistance (1024):
determining when a patient's glottis is closed (1026); and
producing Functional Electric Stimulation (FES) based, at least in part, on the determining (1028);
if the command input corresponds to a command to set parameters (1030):
optionally setting onset of FES relative to onset of glottis closure (1032);
optionally setting duration of FES stimulation (1034);
optionally setting duration of window for sensing when to assist coughing by FES stimulation (1036);
optionally setting power of FES signal (1038); and
optionally setting coughing regime (1040).

Figure 10D:
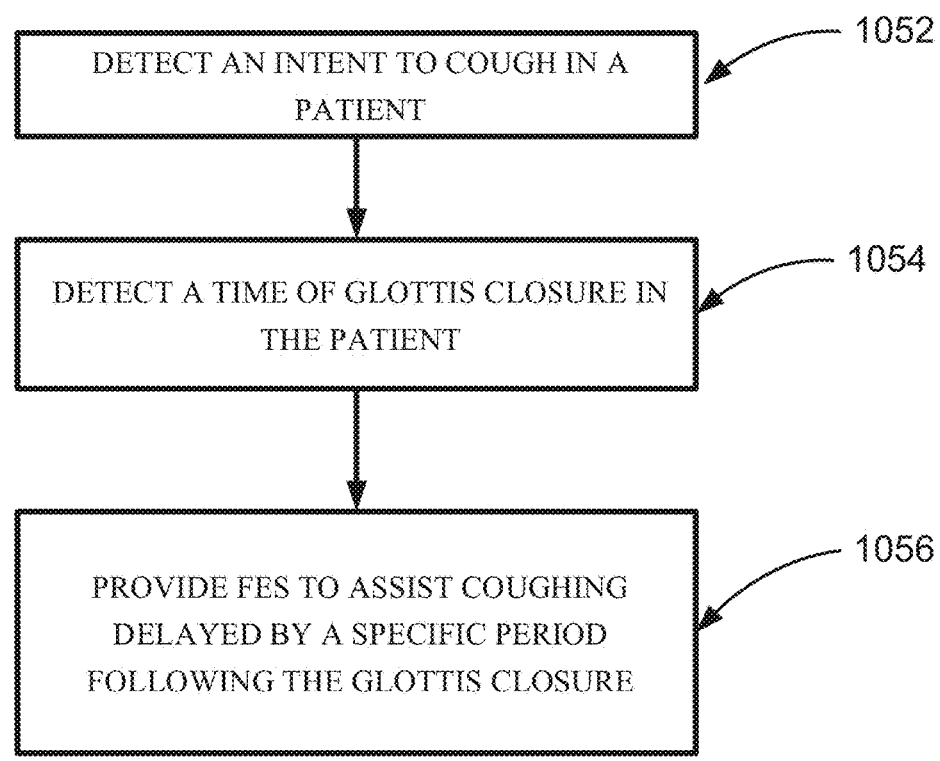
FIG. 10D is a simplified flow chart diagram of a method for providing Functional Electric Stimulation (FES) to assist coughing according to still another example embodiment of the invention.

Reference is now made to FIG. 10D, which is a simplified flow chart diagram of a method for providing Functional Electric Stimulation (FES) to assist coughing according to still another example embodiment of the invention.

FIG. 10D depicts a method including:
detecting an intent to cough in a patient (1052);
detecting a time of glottis closure in the patient (1054);
providing FES to assist coughing delayed by a specific period following the glottis closure (1056).

Respiratory Rehabilitation

In some embodiments, a system of assisted coughing as described herein is optionally used to rehabilitate respiratory action of patients with a weak respiratory action. Use of the system potentially rehabilitates and potentially improves respiratory action in patients.

It is expected that during the life of a patent maturing from this application many relevant air flow sensors, air pressure sensors and electrophysiological sensors will be developed and the scope of the terms air flow sensors, air pressure sensors and electrophysiological sensors is intended to include all such new technologies a priori.

It is expected that during the life of a patent maturing from this application many relevant FES electric signals and electrodes for applying the signals will be developed and the scope of the terms FES electric signals and electrodes for applying the signals is intended to include all such new technologies a priori.

It is expected that during the life of a patent maturing from this application many relevant nasal air flow sensors may be developed and the scope of the term nasal air flow sensor is intended to include all such new technologies a priori.

It is expected that during the life of a patent maturing from this application many relevant EMG sensors may be developed and the scope of the term EMG sensor is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for assisted coughing comprising:
a first air flow sensor configured for sensing a patient's air flow, for measuring a parameter which indicates a closed glottis and producing a first signal;
a processor and associated memory for receiving the first signal, determining a state indicating the closed glottis and generating an instruction for Functional Electric Stimulation (FES) based, at least in part, on the determining; and
a FES controller for generating an electric stimulation signal based on the instruction;
wherein the processor determines a specific point in time associated with the indication of the closed glottis based, at least in part, on detecting a start of a plateau in the first signal.

2. The system of claim 1 in which the processor is further configured for detecting a command input, and to attempt to determine a state indicating closed glottis following the command input.

3. The system of claim 1 in which the first sensor comprises a nasal air sensor configured for sensing the patient's nasal air flow.

4. The system of claim 1 and further comprising a sensor configured to accept a command input.

5. The system of claim 4 in which the sensor configured to accept the command input comprises at least one patient command sensor selected from a group comprising:
the first air flow sensor configured for sensing the patient's nasal air flow:
an eye blink sensor;
a microphone;
an electromyography (EMG) electrode configured for sensing the patient's EMG activity of the neck muscles;
a chest belt for monitoring respiration; and
an electrophysiological sensor for sensing abdominal muscles.

6. A method of assisted coughing comprising:
analyzing a first signal from an air flow sensor configured to sense a patients air flow; determining when a patient's glottis is closed based, at least in part, on the analysis; and
producing Functional Electric Stimulation (FES) based, at least in part, on the determining;
wherein the determining that the patient's glottis is closed is based, at least in part, on determining a specific point in time associated with a start of a plateau in the signal from the air flow sensor.

7. The method of claim 6 in which the determining when the patient's glottis is closed based, at least in part, on analyzing a nasal air signal from the patient's air flow sensor.

8. The method of claim 6 wherein the determining when the patient's glottis is closed is based, at least in part, on determining a slope in the first signal followed by determining a start of a plateau in the first signal, the plateau lasting at least 50 milliseconds.

9. The method of claim 8 and wherein:
a negative slope is fitted to a straight line having a slope $\alpha$;
and the plateau is fitted to a straight line having a slope $\beta$;
a value of $\alpha$ is below a threshold $T\alpha$; and
a value of $\beta$ is below a threshold $T\beta$.

10. The method of claim 9 wherein $\alpha$ and $\beta$ are calculated as follows:

$$\hat{\beta} = \frac{\sum_{i=1}^{n}(x_i - \overline{x})(y_i - \overline{y})}{\sum_{i=1}^{n}(x_i - \overline{x})^2} = \frac{\sum_{i=1}^{n} x_i y_i - \frac{1}{n}\sum_{i=1}^{n} x_i \sum_{j=1}^{n} y_j}{\sum_{i=1}^{n}(x_i^2) - \frac{1}{n}\left(\sum_{i=1}^{n} x_i\right)^2} =$$

$$\frac{\overline{xy} - \overline{x}\,\overline{y}}{\overline{x^2} - \overline{x}^2} = \frac{\text{Cov}[x, y]}{\text{Var}[x]} = r_{xy}\frac{s_y}{s_x}, \hat{\alpha} = \overline{y} - \hat{\beta}\overline{x},$$

where $r_{xy}$ is a sample correlation coefficient between x and y, $s_x$ is a standard deviation of x, $s_y$ is a standard deviation of y, and a horizontal bar over a variable denotes a sample average of the variable.

11. The method of claim 6 in which the determining when the patient's glottis is closed is performed following receipt of a command input.

12. The method of claim 11 in which the receipt of the command input comprises receipt of the command input from a processor analyzing a nasal air flow signal from the patient's air flow sensor.

13. The method of claim 6 and further comprising adjusting the FES.

14. The method of claim 13 in which the adjusting the FES comprises an adjustment selected from a group consisting of:
   adjusting when to start the FES relative to the specific point in time; and
   adjusting a duration of the FES.

15. The method of claim 14 in which the adjusting when to start the FES comprises:
   determining an average duration of a patient's closing the glottis;
   adjusting to start the FES a short period of time prior to an end of the determining when a patient's glottis is expected to be closed.

16. The method of claim 13 in which the adjusting the FES comprises using feedback to adjust the FES.

17. The method of claim 16 in which the feedback comprises at least one parameter selected from a group consisting of:
   a value assigned to the patient's feedback;
   a value assigned to a medical practitioner' feedback;
   a value of air flow temperature during a cough which is assisted by the FES;
   a value of $CO_2$ concentration during a cough which is assisted by the FES;
   a value of electromyography (EMG) measured during a cough which is assisted by the FES;
   a value of PEF (Peak Expiratory Flow) of a cough which is assisted by the FES;
   a value of maximum nasal expiration during the cough which is assisted by the FES;
   a value of maximum volume of a sound of the cough which is assisted by the FES; and
   a value of maximum output of lung air of the cough which is assisted by the FES.

18. The method of claim 6 in which nasal air flow parameters for detecting an intent to cough consists of a value of a slope of air flow data points during inspiration exceeding a threshold value.

19. The method of claim 6 in which the detecting the specific point in time associated with glottis closure in the patient comprises detecting a time when nasal air flow transitions from inspiration to a minimum of air flow.

20. The method of claim 6 and further comprising:
   measuring the patient's glottis closure duration over a plurality of breathing cycles by the patient which include glottis closure and coughing;
   determining a typical glottis closure duration for the patient;
   providing FES to the patient at a time delayed from the specific point in time associated with the start of the plateau, the delay being less than the typical glottis closure duration for the patient.

21. A non-transitory computer-readable medium containing instructions for a method of assisted coughing according to the method of claim 6.

22. A system for assisted coughing comprising:
   a first air flow sensor configured for sensing a patient's air flow, for measuring a parameter which indicates a closed glottis and producing a first signal;
   a processor and associated memory for receiving the first signal, detecting a start of a plateau in the first signal, determining a state indicating the closed glottis, and generating an instruction for Functional Electric Stimulation (FES); and
   a FES controller for generating a FES signal based on the instruction.

* * * * *